(12) United States Patent
Lu et al.

(10) Patent No.: US 8,470,297 B1
(45) Date of Patent: *Jun. 25, 2013

(54) FDG-PET EVALUATION OF EWING'S SARCOMA SENSITIVITY

(75) Inventors: Brian DerHua Lu, Westfield, NJ (US); Siu-Long Yao, West Windsor, NJ (US); Cynthia Seidel-Dugan, Mountainside, NJ (US); Yan Wang, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 283 days.

This patent is subject to a terminal disclaimer.

(21) Appl. No.: 12/879,359

(22) Filed: Sep. 10, 2010

Related U.S. Application Data

(60) Provisional application No. 61/241,137, filed on Sep. 10, 2009.

(51) Int. Cl.
*A61K 51/00* (2006.01)
*A61M 36/14* (2006.01)

(52) U.S. Cl.
USPC ....... 424/1.89; 424/1.11; 424/1.65; 424/1.69; 424/1.73; 424/1.81; 424/9.1; 424/9.4; 514/1.1

(58) Field of Classification Search
USPC ................ 424/1.11, 1.49, 1.65, 1.69, 1.81, 424/1.85, 1.89, 9.1, 9.3, 9.4, 9.5, 9.6, 9.7, 424/9.8, 1.73; 534/7, 10–16; 514/1, 1.1; 530/300, 303, 350, 351, 387.1, 387.3, 387.7, 530/387.9, 388.1, 388.15, 388.23, 388.24
See application file for complete search history.

(56) References Cited

U.S. PATENT DOCUMENTS

| | | | |
|---|---|---|---|
| 7,217,796 B2 | 5/2007 | Wang et al. |
| 7,241,444 B2 | 7/2007 | Goetsch et al. |
| 7,553,485 B2 | 6/2009 | Goetsch et al. |
| 7,667,021 B2 | 2/2010 | Wang et al. |
| 7,847,068 B2 | 12/2010 | Wang et al. |
| 7,851,181 B2 | 12/2010 | Wang et al. |
| 7,914,784 B2 | 3/2011 | Goetsch et al. |
| 8,101,180 B2 | 1/2012 | Goetsch et al. |
| 8,168,410 B2 | 5/2012 | Goetsch et al. |
| 8,173,779 B2 | 5/2012 | Wang et al. |
| 2005/0084906 A1 | 4/2005 | Goetsch et al. |
| 2005/0249730 A1 | 11/2005 | Goetsch et al. |
| 2008/0063639 A1 | 3/2008 | Goetsch et al. |
| 2008/0193445 A1 | 8/2008 | Goetsch et al. |
| 2008/0286198 A1 | 11/2008 | Goetsch et al. |
| 2011/0014122 A1 | 1/2011 | Goetsch et al. |
| 2011/0183376 A1 | 7/2011 | Goetsch et al. |
| 2012/0208721 A1 | 8/2012 | Goetsch et al. |

FOREIGN PATENT DOCUMENTS

| | | |
|---|---|---|
| WO | WO03/059951 | 7/2003 |
| WO | WO03/100008 | 12/2003 |

*Primary Examiner* — D L Jones

(57) ABSTRACT

This invention relates to methods for evaluating the efficacy of an IGF1R inhibitor, such as an anti-IGF1R antibody, for the treatment of an Ewing's sarcoma tumor by determining the level of tumoral glucose metabolism. Tumoral glucose metabolism is determining at an early point in the treatment regimen by any of several methods known in the art including FDG-PET/CT scan.

21 Claims, No Drawings

FDG-PET EVALUATION OF EWING'S SARCOMA SENSITIVITY

This Application claims the benefit of U.S. provisional patent application No. 61/241,137; filed Sep. 10, 2009; which is herein incorporated by reference in its entirety.

FIELD OF THE INVENTION

The field of the invention relates, generally, to methods for treatment of patients with tumors with an IGF1R inhibitor wherein the tumors have been evaluated by PET scan for sensitivity to the inhibitor.

BACKGROUND OF THE INVENTION

Early prediction of response to a chemotherapeutic treatment is of great value to avoid unnecessary toxicity of ineffective treatment and to get a chance to receive another effective treatment at an early stage.

Increased uptake of $^{18}$F-fluorodeoxyglucose (FDG) measured by positron emission tomography (PET) reflects glucose metabolism and proliferative activity of tumor cells. Metabolic imaging with FDG-PET has been used for staging, restaging, and evaluating treatment efficacy in various cancers. Some studies have indicated that FDG-PET is useful for the early evaluation of tumor response to anticancer drugs.

FDG-PET has been used to predict chemotherapeutic efficacy of Ewing's sarcoma tumors. However, the value of FDG-PET scans performed at an early point in a treatment regimen has not been heretofore realized. Specifically, whether the observation of an effect on tumor metabolism (or lack of an effect) at an early point will predict overall sensitivity of the tumor to a given therapy is uncertain. Clearly, a study that clarifies this uncertainty would be useful and would suggest a new method for quick evaluation of Ewing's sarcoma tumor sensitivity.

SUMMARY OF THE INVENTION

The present invention addressed this need by providing a method for making an early determination as to the efficacy of an IGF1R inhibitor treatment regimen for Ewing's sarcoma by way of an FDG-PET analysis of the tumor.

The present invention provides, in part, a method for treating a Ewing's sarcoma tumor (e.g., recurrent or relapsed Ewing's sarcoma), in a subject (e.g., a human), comprising evaluating glucose metabolism of the tumor after the subject has received a first dose of IGF1R inhibitor (e.g., an isolated antibody or antigen-binding fragment thereof such as an isolated antibody or antigen-binding fragment thereof comprising CDR-H1, CDR-H2 and CDR-H3 of the heavy chain immunoglobulin variable region whose amino acid sequence is set forth in SEQ ID NO: 10, 12, 13, 14, 15, 16, 17 or 18; and CDR-L1, CDR-L2 and CDR-L3 of the light chain immunoglobulin variable region whose amino acid sequence is set forth in SEQ ID NO: 2, 4, 6, 8, 19, 20, 21, 22, 23 or 24; e.g., wherein the antibody or fragment heavy and/or light chain variable region is linked to an immunoglobulin constant domain such as for example, a kappa light chain, a lambda light chain, a gamma-1 heavy chain, a gamma-2 heavy chain, a gamma-3 heavy chain and/or a gamma-4 heavy chain), but before a second dose of the inhibitor; or within 14 days of a first dose of IGF1R inhibitor but before a second dose of said inhibitor; wherein treatment with the IGF1R inhibitor is discontinued if glucose metabolism does not significantly decrease or remain constant after said first dose; and continuing treatment with the IGF1R inhibitor if glucose metabolism does significantly decrease or remain constant after said first dose. Similar methods for determining if a Ewing's sarcoma tumor is sensitive to an IGF1R inhibitor; for selecting a patient for treatment with an IGF1R inhibitor; for identifying a patient with an IGF1R sensitive tumor; and for evaluating dosage of an IGF1R inhibitor are encompassed by the present invention. These methods are discussed in greater detail herein, e.g., below under the "Biomarkers" section. In an embodiment of the invention, glucose metabolism is evaluated by administering labeled glucose and monitoring its metabolism by the tumor, for example, wherein glucose metabolism is evaluated by $^{18}$F-fluorodeoxyglucose positron emission tomography (FDG-PET). In an embodiment of the invention, the method comprises the step of continuing treatment with the IGF1R inhibitor if glucose metabolism decreases by about 15% to about 25% after said first dose. In an embodiment of the invention, the subject is administered an IGF1R antibody (e.g., as discussed herein) at a dose of about 1 to about 20 mg/kg every two weeks; e.g., about 10 mg/kg every two weeks). In an embodiment of the invention, the subject is administered the IGF1R inhibitor in association with a further chemotherapeutic agent such as aprepitant and/or any other further chemotherapeutic agent discussed herein, for example, below under the "Further chemotherapeutic agents" section.

DETAILED DESCRIPTION OF THE INVENTION

The present invention provides a method for evaluating whether a Ewing's sarcoma tumor will be sensitive to an IGF1R inhibitor. The method includes evaluating the tumor's metabolism of FDG via PET scan. Data presented herein established that a reduction in FDG metabolism, as measured by PET scan, when performed within one to two weeks of initial treatment, is highly predictive of the sensitivity of the tumor for the IGF1R inhibitor.

Biomarkers

The present invention encompasses a method for treating a Ewing's sarcoma tumor, in a subject, comprising evaluating glucose metabolism of the tumor after the subject has received a first dose of IGF1R inhibitor, but before a second dose of the inhibitor; or within 14 days of a first dose of IGF1R inhibitor (e.g., 7-14 days, 7-10 days, 1 days, 2 days, 3 days, 4 days, 5 days, 6 days, 7 days, 8 days, 9 days, 10 days, 11 days, 12 days, 13 days or 14 days) but before a second dose of said inhibitor; wherein treatment with the IGF1R inhibitor (e.g., an isolated anti-IGF1R antibody such as any of those discussed herein) is discontinued if glucose metabolism does not significantly decrease or remain constant after said first dose (e.g., as compared to the level of glucose metabolism before the first dose); and continuing treatment with the IGF1R inhibitor if glucose metabolism does significantly decrease or remain constant after said first dose (e.g., as compared to the level of glucose metabolism before the first dose).

For example, in an embodiment of the present invention, the step of evaluating and comparing glucose metabolism of the tumor in a subject receiving an IGF1R inhibitor treatment regimen includes the steps of:
(i) administering the radiolabeled glucose to a subject, e.g., FDG (e.g., about 10 to about 20 mCi, e.g., about 10 mCi, about 11 mCi, about 12 mCi, about 13 mCi, about 14 mCi, about 15 mCi, about 16 mCi, about 17 mCi, about 18 mCi, about 19 mC or about 20 mCi), for example via intravenous injection; and
(ii) allowing the radiolabeled glucose to incubate for about 75 minutes;
(iii) PET scanning or PET/CT scanning at least part of the subject's body, e.g., a whole body scan from skull base to proximal femurs; and
(iv) identifying and evaluating any detected levels of tumoral glucose metabolism in the subject.

If the levels of tumoral glucose metabolism before and after initial treatment with an IGF1R inhibitor are to be compared, the following further steps can be performed:
(a) administering a first dose of the IGF1R inhibitor (e.g., 10 mg/kg of anti-IGF1R antibody) to the subject;
(b) waiting about 7-14 days (e.g., 7-14 days, 7-10 days, 1 days, 2 days, 3 days, 4 days, 5 days, 6 days, 7 days, 8 days, 9 days, 10 days, 11 days, 12 days, 13 days or 14 days; but before any second dose is administered) or until a second dose is due under the selected anti-IGF1R treatment regimen; then re-evaluating glucose metabolism by any tumor detected in the first scan(s), e.g., by:
(1) administering the radiolabeled glucose to a subject, e.g., FDG (e.g., about 10 to about 20 mCi, e.g., about 10 mCi, about 11 mCi, about 12 mCi, about 13 mCi, about 14 mCi, about 15 mCi, about 16 mCi, about 17 mCi, about 18 mCi, about 19 mC or about 20 mCi), for example via intravenous injection; and
(2) allowing the radiolabeled glucose to incubate for about 75 minutes;
(3) PET scanning or PET/CT scanning at least part of the subject's body, e.g., a whole body scan from skull base to proximal femurs;
(4) identifying and evaluating any detected levels of FDG metabolism in the subject;
(5) comparing the levels of glucose metabolism detected before and after the first dose of IGF1R inhibitor.

FDG-PET scans are well known techniques in the art and are well within the abilities of a practitioner of ordinary skill in the art.

In an embodiment of the invention, a significant decrease in glucose (e.g., FDG) metabolism is any measurable amount of decrease that would be recognized by a practitioner of ordinary skill in the art, under the circumstances and in view of the particularities of the patient or subject's clinical state, would recognize as significant. In an embodiment of the invention, a significant decrease is between about 15% and about 25% (e.g., about 15-20%, about 15-25%, about 20-25%, about 15%, about 16%, about 17%, about 18%, about 19%, about 20%, about 21%, about 22%, about 23%, about 24%, about 25%).

The magnitude of radioactivity (e.g., when using an FDG marker) in a tumor cell can be converted from PET signal to absolute radiation units (e.g., using methods commonly known in the art) when evaluating whether a decrease of glucose metabolism has occurred. Alternatively, arbitrary units of PET signal are merely compared when determining whether a decrease in glucose metabolism has occurred. In an embodiment of the invention, tumor-to-background ratios of FDG uptake are compared when making a determination as to whether a decrease of glucose metabolism has occurred.

The present invention further encompasses a method for evaluating whether a Ewing's sarcoma tumor is sensitive to an IGF1R inhibitor comprising evaluating glucose metabolism of the tumor after the subject has received a first dose of IGF1R inhibitor, but before a second dose of the inhibitor; or within 14 days of a first dose of IGF1R inhibitor (e.g., 7-14 days, 7-10 days, 1 days, 2 days, 3 days, 4 days, 5 days, 6 days, 7 days, 8 days, 9 days, 10 days, 11 days, 12 days, 13 days or 14 days) but before a second dose of said inhibitor; wherein the tumor is determined to be insensitive to the IGF1R inhibitor (e.g., an isolated anti-IGF1R antibody such as any of those discussed herein) if glucose metabolism does not significantly decrease or remain constant after said first dose (e.g., as compared to the level of glucose metabolism before the first dose); and wherein the tumor is determined to be sensitive to the IGF1R inhibitor if glucose metabolism does significantly decrease or remain constant after said first dose (e.g., as compared to the level of glucose metabolism before the first dose).

The present invention further encompasses a method for evaluating dosage of an IGF1R inhibitor for treatment of a Ewing's sarcoma tumor comprising evaluating glucose metabolism of the tumor after the subject has received a first dose of IGF1R inhibitor, but before a second dose of the inhibitor; or within 14 days of a first dose of IGF1R inhibitor (e.g., 7-14 days, 7-10 days, 1 days, 2 days, 3 days, 4 days, 5 days, 6 days, 7 days, 8 days, 9 days, 10 days, 11 days, 12 days, 13 days or 14 days) but before a second dose of said inhibitor; wherein the dose is determined to be too low if glucose metabolism does not significantly decrease or remain constant after said first dose (e.g., as compared to the level of glucose metabolism before the first dose); and wherein the dose is determined to be sufficient if glucose metabolism does significantly decrease or remain constant after said first dose (e.g., as compared to the level of glucose metabolism before the first dose).

The present invention further encompasses a method for identifying a subject with a Ewing's sarcoma tumor that is sensitive to an IGF1R inhibitor comprising evaluating glucose metabolism of the tumor after the subject has received a first dose of IGF1R inhibitor, but before a second dose of the inhibitor; or within 14 days of a first dose of IGF1R inhibitor (e.g., 7-14 days, 7-10 days, 1 days, 2 days, 3 days, 4 days, 5 days, 6 days, 7 days, 8 days, 9 days, 10 days, 11 days, 12 days, 13 days or 14 days) but before a second dose of said inhibitor; wherein the subject is identified as having an insufficiently sensitive or insensitive tumor if glucose metabolism does not significantly decrease or remain constant after said first dose (e.g., as compared to the level of glucose metabolism before the first dose); and wherein the subject is identified as having a sufficiently sensitive tumor if glucose metabolism does significantly decrease or remain constant after said first dose (e.g., as compared to the level of glucose metabolism before the first dose).

A method for selecting a subject with a Ewing's sarcoma tumor for receipt of an IGF1R inhibitor treatment of the tumor comprising evaluating glucose metabolism of the tumor after the subject has received a first dose of IGF1R inhibitor, but before a second dose of the inhibitor; or within 14 days of a first dose of IGF1R inhibitor (e.g., 7-14 days, 7-10 days, 1 days, 2 days, 3 days, 4 days, 5 days, 6 days, 7 days, 8 days, 9 days, 10 days, 11 days, 12 days, 13 days or 14 days) but before a second dose of said inhibitor; wherein the subject is not selected if glucose metabolism does not significantly decrease or remain constant after said first dose (e.g., as compared to the level of glucose metabolism before the first dose); and wherein the subject is selected if glucose metabolism does significantly decrease or remain constant after said first dose (e.g., as compared to the level of glucose metabolism before the first dose).

IGF1R Inhibitors

The terms "IGF1R inhibitor" or "IGF1R antagonist" or the like include any substance that decreases the expression, ligand binding (e.g., binding to IGF-1 and/or IGF-2), kinase activity (e.g., autophosphorylation activity) or any other biological activity of IGF1R (e.g., mediation of anchorage-independent cellular growth) e.g., that will elicit a biological or medical response of a tissue, system, subject or patient that is being sought by the administrator (such as a researcher, doctor or veterinarian) which includes any measurable alleviation of the signs, symptoms and/or clinical indicia of cancer (e.g., tumor growth) and/or the prevention, slowing or halting of progression or metastasis of cancer to any degree.

In an embodiment of the invention, the IGF1R inhibitor is any isolated antibody or antigen-binding fragment thereof that binds specifically to insulin-like growth factor-1 receptor (e.g., human IGF1R) or any soluble fragment thereof (e.g., monoclonal antibodies (e.g., fully human monoclonal antibodies), polyclonal antibodies, bispecific antibodies, Fab antibody fragments, F(ab)₂ antibody fragments, Fv antibody fragments (e.g., VH or VL), single chain Fv antibody fragments, dsFv antibody fragments, humanized antibodies or chimeric antibodies) such as any of those disclosed in any of Burtrum et. al Cancer Research 63:8912-8921 (2003); in French Patent Applications FR2834990, FR2834991 and FR2834900 and in PCT Application Publication Nos. WO 03/100008; WO 03/59951; WO 04/71529; WO 03/106621; WO 04/83248; WO 04/87756, WO 05/16970; and WO 02/53596.

In an embodiment of the invention, an IGF1R inhibitor is an isolated anti-insulin-like growth factor-1 receptor (IGF1R) antibody comprising a mature 19D12/15H12 Light Chain (LC)—C, D, E or F and a mature 19D12/15H12 heavy chain (HC)-A or B (e.g., mature LCB/mature HCB, mature LCC/mature HCB or mature LCF/mature HCA). In an embodiment of the invention, an IGF1R inhibitor that is administered to a patient in a method according to the invention is an isolated antibody that specifically binds to IGF1R that comprises one or more complementarity determining regions (CDRs) of 19D12/15H12 Light Chain-C, D, E or F and/or 19D12/15H12 heavy chain-A or B (e.g., all 3 light chain CDRs and/or all 3 heavy chain CDRs). In an embodiment of the invention, the IGF1R inhibitor is an anti-IGF1R antibody which is robatumumab or MK-0646 (dalotuzumab).

The amino acid and nucleotide sequences of the some immunoglobulin chains of the invention are shown below. Dotted, underscored type indicates the signal peptide. Solid underscored type indicates the CDRs. Plain type indicates the framework regions. Mature fragments lack the signal peptide.

```
Modified 19D12/15H12 Light Chain-C
                                                    (SEQ ID NO: 1)
ATG TCG CCA TCA CAA CTC ATT GGG TTT CTG CTG CTC TGG GTT CCA GCC TCC

AGG GGT GAA ATT GTG CTG ACT CAG AGC CCA GAC TCT CTG TCT GTG ACT CCA

GGC GAG AGA GTC ACC ATC ACC TGC CGG GCC AGT CAG AGC ATT GGT AGT AGC

TTA CAC TGG TAC CAG CAG AAA CCA GGT CAG TCT CCA AAG CTT CTC ATC AAG

TAT GCA TCC CAG TCC CTC TCA GGG GTC CCC TCG AGG TTC AGT GGC AGT GGA

TCT GGG ACA GAT TTC ACC CTC ACC ATC AGT AGC CTC GAG GCT GAA GAT GCT

GCA GCG TAT TAC TGT CAT CAG AGT AGT CGT TTA CCT CAC ACT TTC GGC CAA

GGG ACC AAG GTG GAG ATC AAA CGT ACG
```

```
                                                    (SEQ ID NO: 2)
         M S P S Q L I G F L L L W V P A S

R G E I V L T Q S P D S L S V T P

G E R V T I T C R A S Q S I G S S

L H W Y Q Q K P G Q S P K L L I K

Y A S Q S L S G V P S R F S G S G

S G T D F T L T I S S L E A E D A

A A Y Y C H Q S S R L P H T F G Q

G T K V E I K R T
```

```
Modified 19D12/15H12 Light Chain-D
                                                    (SEQ ID NO: 3)
ATG TCG CCA TCA CAA CTC ATT GGG TTT CTG CTG CTC TGG GTT CCA GCC TCC

AGG GGT GAA ATT GTG CTG ACT CAG AGC CCA GAC TCT CTG TCT GTG ACT CCA

GGC GAG AGA GTC ACC ATC ACC TGC CGG GCC AGT CAG AGC ATT GGT AGT AGC

TTA CAC TGG TAC CAG CAG AAA CCA GGT CAG TCT CCA AAG CTT CTC ATC AAG

TAT GCA TCC CAG TCC CTC TCA GGG GTC CCC TCG AGG TTC AGT GGC AGT GGA
```

```
TCT GGG ACA GAT TTC ACC CTC ACC ATC AGT AGC CTC GAG GCT GAA GAT TTC

GCA GTG TAT TAC TGT CAT CAG AGT AGT CGT TTA CCT CAC ACT TTC GGC CAA

GGG ACC AAG GTG GAG ATC AAA CGT ACG
```

(SEQ ID NO: 4)

M S P S Q L I G F L L L W V P A S
R G E I V L T Q S P D S L S V T P
G E R V T I T C R A S Q S I G S S
L H W Y Q Q K P G Q S P K L L I K
Y A S Q S L S G V P S R F S G S G
S G T D F T L T I S S L E A E D F
A V Y Y C H Q S S R L P H T F G Q
G T K V E I K R T

Modified 19D12/15H12 Light Chain-E
(SEQ ID NO: 5)
```
ATG TCG CCA TCA CAA CTC ATT GGG TTT CTG CTG CTC TGG GTT CCA GCC TCC

AGG GGT GAA ATT GTG CTG ACT CAG AGC CCA GGT ACC CTG TCT GTG TCT CCA

GGC GAG AGA GCC ACC CTC TCC TGC CGG GCC AGT CAG AGC ATT GGT AGT AGC

TTA CAC TGG TAC CAG CAG AAA CCA GGT CAG GCT CCA AGG CTT CTC ATC AAG

TAT GCA TCC CAG TCC CTC TCA GGG ATC CCC GAT AGG TTC AGT GGC AGT GGA

TCT GGG ACA GAT TTC ACC CTC ACC ATC AGT AGA CTG GAG CCT GAA GAT GCT

GCA GCG TAT TAC TGT CAT CAG AGT AGT CGT TTA CCT CAC ACT TTC GGC CAA

GGG ACC AAG GTG GAG ATC AAA CGT ACA
```

(SEQ ID NO: 6)

M S P S Q L I G F L L L W V P A S
R G E I V L T Q S P G T L S V S P
G E R A T L S C R A S Q S I G S S
L H W Y Q Q K P G Q A P R L L I K
Y A S Q S L S G I P D R F S G S G
S G T D F T L T I S R L E P E D A
A A Y Y C H Q S S R L P H T F G Q
G T K V E I K R T

Modified 19D12/15H12 Light Chain-F
(SEQ ID NO: 7)
```
ATG GAG TTT GGG CTG AGC TGG GTT TTC CTT GTT GCT ATA TTA AAA GGT GTC

CAG TGT GAA ATT GTG CTG ACT CAG AGC CCA GGT ACC CTG TCT GTG TCT CCA

GGC GAG AGA GCC ACC CTC TCC TGC CGG GCC AGT CAG AGC ATT GGT AGT AGC

TTA CAC TGG TAC CAG CAG AAA CCA GGT CAG GCT CCA AGG CTT CTC ATC AAG

TAT GCA TCC CAG TCC CTC TCA GGG ATC CCC GAT AGG TTC AGT GGC AGT GGA

TCT GGG ACA GAT TTC ACC CTC ACC ATC AGT AGA CTG GAG CCT GAA GAT TTC
```

-continued

GCA GTG TAT TAC TGT <u>CAT CAG AGT AGT CGT TTA CCT CAC ACT</u> TTC GGC CAA

GGG ACC AAG GTG GAG ATC AAA CGT ACA (SEQ ID NO: 8)
<u>M</u> S P S Q L I G F L L L <u>W</u> V P A S

<u>R G</u> E I V L T Q S P G T L S V S P

G E R A T L S C <u>R A S Q S I G S S</u>

<u>L H</u> W Y Q Q K P G Q A P R L L I K

-continued

<u>Y A S Q S L S</u> G I P D R F S G S G

S G T D F T L T I S R L E P E D F

A V Y Y C <u>H Q S S R L P H T</u> F G Q

G T K V E I K R T

Modified 19D12/15H12 heavy chain-A
(SEQ ID NO: 9)
<u>ATG GAG TTT GGG CTG AGC TGG GTT TTC CTT GTT GCT ATA TTA AAA GGT GTC</u>

<u>CAG TGT</u> GAG GTT CAG CTG GTG CAG TCT GGG GGA GGC TTG GTA AAG CCT GGG

GGG TCC CTG AGA CTC TCC TGT GCA GCC TCT GGA TTC ACC TTC AGT <u>AGC TTT</u>

<u>GCT ATG CAC</u> TGG GTT CGC CAG GCT CCA GGA AAA GGT CTG GAG TGG ATA TCA

<u>GTT ATT GAT ACT CGT GGT GCC ACA TAC TAT GCA GAC TCC GTG AAG GGC</u> CGA

TTC ACC ATC TCC AGA GAC AAT GCC AAG AAC TCC TTG TAT CTT CAA ATG AAC

AGC CTG AGA GCC GAG GAC ACT GCT GTG TAT TAC TGT GCA AGA <u>CTG GGG AAC</u>

<u>TTC TAC TAC GGT ATG GAC GTC</u> TGG GGC CAA GGG ACC ACG GTC ACC GTC TCC

TCA (SEQ ID NO: 10)
<u>Met Glu Phe Gly Leu Ser Trp Val Phe Leu Val Ala Ile Leu Lys Gly Val</u>

<u>Gln Cys</u> Glu Val Gln Leu Val Gln Ser Gly Gly Gly Leu Val Lys Pro Gly

Gly Ser Leu Arg Leu Ser Cys Ala Ala Ser Gly Phe Thr Phe Ser <u>Ser Phe</u>

<u>Ala Met His</u> Trp Val Arg Gln Ala Pro Gly Lys Gly Leu Glu Trp Ile Ser

<u>Val Ile Asp Thr Arg Gly Ala Thr Tyr Tyr Ala Asp Ser Val Lys Gly</u> Arg

Phe Thr Ile Ser Arg Asp Asn Ala Lys Asn Ser Leu Tyr Leu Gln Met Asn

Ser Leu Arg Ala Glu Asp Thr Ala Val Tyr Tyr Cys Ala Arg <u>Leu Gly Asn</u>

<u>Phe Tyr Tyr Gly Met Asp Val</u> Trp Gly Gln Gly Thr Thr Val Thr Val Ser

Ser

Modified 19D12/15H12 heavy chain-B
(SEQ ID NO: 11)
<u>ATG GAG TTT GGG CTG AGC TGG GTT TTC CTT GTT GCT ATA TTA AAA GGT GTC</u>

<u>CAG TGT</u> GAG GTT CAG CTG GTG CAG TCT GGG GGA GGC TTG GTA CAG CCC GGG

GGG TCC CTG AGA CTC TCC TGT GCA GCC TCT GGA TTC ACC TTC AGT <u>AGC TTT</u>

<u>GCT ATG CAC</u> TGG GTT CGC CAG GCT CCA GGA AAA GGT CTG GAG TGG ATA TCA

<u>GTT ATT GAT ACT CGT GGT GCC ACA TAC TAT GCA GAC TCC GTG AAG GGC</u> CGA

TTC ACC ATC TCC AGA GAC AAT GCC AAG AAC TCC TTG TAT CTT CAA ATG AAC

-continued

```
AGC CTG AGA GCC GAG GAC ACT GCT GTG TAT TAC TGT GCA AGA CTG GGG AAC

TTC TAC TAC GGT ATG GAC GTC TGG GGC CAA GGG ACC ACG GTC ACC GTC TCC

TCA
```

(SEQ ID NO: 12)
Met Glu Phe Gly Leu Ser Trp Val Phe Leu Val Ala Ile Leu Lys Gly Val

Gln Cys Glu Val Gln Leu Val Gln Ser Gly Gly Gly Leu Val Gln Pro Gly

Gly Ser Leu Arg Leu Ser Cys Ala Ala Ser Gly Phe Thr Phe Ser Ser Phe

Ala Met His Trp Val Arg Gln Ala Pro Gly Lys Gly Leu Glu Trp Ile Ser

Val Ile Asp Thr Arg Gly Ala Thr Tyr Tyr Ala Asp Ser Val Lys Gly Arg

Phe Thr Ile Ser Arg Asp Asn Ala Lys Asn Ser Leu Tyr Leu Gln Met Asn

Ser Leu Arg Ala Glu Asp Thr Ala Val Tyr Tyr Cys Ala Arg Leu Gly Asn

Phe Tyr Tyr Gly Met Asp Val Trp Gly Gln Gly Thr Thr Val Thr Val Ser

Ser

Plasmids comprising a CMV promoter operably linked to the 15H12/19D12 light chains and heavy chains have been deposited at the American Type Culture Collection (ATCC); 10801 University Boulevard; Manassas, Va. 20110-2209 on May 21, 2003. The deposit name and the ATCC accession numbers for the cell lines are set forth below:

CMV promoter-15H12/19D12 LCC (κ)—
 Deposit name: "15H12/19D12 LCC (κ)";
 ATCC accession No.: PTA-5217
CMV promoter-15H12/19D12 LCD (κ)—
 Deposit name: "15H12/19D12 LCD (κ)";
 ATCC accession No.: PTA-5218
CMV promoter-15H12/19D12 LCE (κ)—
 Deposit name: "15H12/19D12 LCE (κ)";
 ATCC accession No.: PTA-5219
CMV promoter-15H12/19D12 LCF (κ)—
 Deposit name: "15H12/19D12 LCF (κ)";
 ATCC accession No.: PTA-5220
CMV promoter-15H12/19D12 HCA (γ4)—
 Deposit name: "15H12/19D12 HCA (γ4)"
 ATCC accession No.: PTA-5214
CMV promoter-15H12/19D12 HCB (γ4)—
 Deposit name: "15H12/19D12 HCB (γ4)"
 ATCC accession No.: PTA-5215
CMV promoter-15H12/19D12 HCA (γ1)—
 Deposit name: "15H12/19D12 HCA (γ1)";
 ATCC accession No.: PTA-5216

The present invention includes methods (e.g., any disclosed herein) comprising administration of anti-IGF1R antibodies and antigen-binding fragments thereof comprising any of the light and/or heavy immunoglobulin chains or mature fragments thereof located in any of the foregoing plasmids deposited at the ATCC.

Other variable heavy and light chain immunoglobulins of anti-IGF1R antibodies and antigen-binding fragments thereof that may be used in method of the present invention are as follows:

```
                                     VH domains
(1) EVQLVQSGGGLVHPGGSLRLSCAGS GFTFRNYAMY WVRQAPGKGLEWVS AIG-SGGGTYYADSVKG
(2) QVELVESGGGVVQPGRSQRLSCAAS GFTFSSYGMH WVRQAPGKGLEWVA IIWFDGSSTYYADSVRG
(3) EVQLLESGGGLVQPGGSLRLSCTAS GFTESSYAMN WVRQAPGKGLEWVS AISGSGGTTFYADSVKG
(4) EVQLVQSGAEVKKPGSSVKVSCKAS GGTFSSYAIS WVRQAPGQGLEWMG GIIPIFGTANYAQKFQG
(5) QVQLQESGPGLVKPSGTLSLTCAVS GGSISSSNWWS WVRQPPGKGLEWIG EIY-HSGSTNYNPSLKS
(6) QVQLQESGPGLVKPSETLSLTCTVS GYSISGGYLWN WIRQPPGKGLEWIG YTS-YDGTNNYKPSLKD (1) RFTISRDNAKNSLYLQMNSLRAEDMAVYYCAR APNWGSDA----------FDI WGQGTMVTVSS
(2) RFTISRDNSKNTLYLQMNSLRAEDTAVYFCAR ELGRR------------YFDL WGRGTLVSVSS
(3) RFTISRDNSRTTLYLQMNSLRAEDTAVYYCAK DLGWSDS-----YYYYYGMDV WGQGTTVTVSS
(4) RVTITADKSTSTAYMELSSLRSEDTAVYYCAR APLRFLEWSTQDRYYYYKDV WGKGTTVTVSS
(5) RVTISVDKSKNQFSLKLSSVTAADTAVYYCAR WTGRTD-----------AFDI WGQGTWVTVSS
(6) RVTISVDTSKNQFSLKLSSVTAADTAVYYCAR YGRV-------------FFDY WGQGTLVTVSS
1 = SEQ ID NO: 13
2 = SEQ ID NO: 14
3 = SEQ ID NO: 15
4 = SEQ ID NO: 16
5 = SEQ 1D NO: 17
6 = SEQ ID NO: 18
```

-continued

VL Domains

```
(a) DIQMTQSPSSLSASVGDRVTITC  RASQGISSWLA       WYQQKPEKAPKSLIY  AASSLQS
(b) EIVLTQSPATLSLSPGERATLSC  RASQSVSSYLA       WYQQKPGQAPRLLIY  DASKRAT
(c) DIQMTQFPSSLSASVGDRVTITC  RASQGIRNDLG       WYQQKPGKAPKRLIY  AASRLHR
(d) SSELTQDP-AVSVALGQTVRITC  QGDSLRSYYAT       WYQQKPGQAPILVIY  GENKRPS
(e) DVVMTQSPLSLPVTPGEPASISC  RSSQSLLHSNGYNYLD  WYLQKPGQSPQLLIY  LGSNRAS
(f) DIVMTQSPLSLPVTPGEPASISC  RSSQSIVHSNGNTYLQ  WYLQKPGQSPQLLIY  KVSNRLY (a) GVPSRFSGSGSGTDFTLTISSLQPEDFATYYC  QQYNSYPPT   FGPGTKVDIK
(b) GIPARFSGSGSGTDFTLTISSLEPEDFAVYYC  QQRSKWPPWT  FGQGTKVESK
(C) GVPSRFSGSGSGTEFTLTISSLQPEDFATYYC  LQHNSYPCS   FGQGTKLEIKRT
(d) GIPARFSGSSSGNTASLTITGAGAEDEADYYC  KSRDGSGQHLV FGGGTKLTVLG
(e) GVPDRFSGSGSGTDFTLKISRVEAEDVGVYYC  MQGTHWPLT   FGQGTKVEIK
(f) GVPDRFSGSGSGTDFTLKISRVEAEDVGVYYC  FQGSHVPWT   FGQGTKVEIK
a = SEQ ID NO: 19
b = SEQ ID NO: 20
c = SEQ ID NO: 21
d = SEQ ID NO: 22
e = SEQ ID NO: 23
f = SEQ ID NO: 24
```

In an embodiment of the invention, $V_H1$ is paired, in an antibody or antigen-binding fragment thereof, with $V_L a$; $V_H2$ is paired, in an antibody or antigen-binding fragment thereof, with $V_L b$; $V_H3$ is paired, in an antibody or antigen-binding fragment thereof, with $V_L c$; $V_H4$ is paired, in an antibody or antigen-binding fragment thereof, with $V_L d$; $V_H5$ is paired, in an antibody or antigen-binding fragment thereof, with $V_L e$; and/or $V_H6$ is paired, in an antibody or antigen-binding fragment thereof, with $V_L f$. Methods comprising use of an anti-IGF1R comprising one or more CDRs (e.g., 3 light chain CDRs and/or 3 heavy chain CDRs) from the variable regions set forth herein (e.g., (a)-(f) set forth above) are also included within the scope of the present invention.

Positron Emission Tomography (PET)/Computed Tomography (CT)

Positron emission tomography (PET) is a nuclear medicine imaging technique which produces an image or picture (e.g., in 3 dimensions) of functional processes in the body. The system detects pairs of gamma rays emitted indirectly by a positron-emitting radionuclide (tracer), which is introduced into the body on a biologically active molecule. Images of tracer concentration (e.g., in 3-dimensional space) within the body can be reconstructed by computer analysis. In modern scanners, this reconstruction is often accomplished with the aid of a CT X-ray scan performed on the patient during the same session, in the same machine.

A typical tracer is the biologically active molecule FDG, an analogue of glucose. FDG is [$^{18}$F]-fluorodeoxyglucose. The concentrations of tracer imaged reflect tissue metabolic activity, in terms of regional glucose uptake. Although use of this tracer results in the most common type of PET scan, other tracer molecules are used in PET to image the tissue concentration of many other types of molecules of interest.

"CT" stands for computed tomography. CT uses x-rays and a computer to make an image of sections of your body. A CT scan shows a subject's organs, bones, and tissues in greater detail than regular x-rays do. For a CT scan, the subject will, generally, receive a contrast enhancing agent by intravenous line (IV), which helps produce an even clearer image. CT exposes the subject to a small amount of radiation.

A PET/CT is an imaging tool combines 2 different types of imaging into 1 procedure. PET and CT together produce a more accurate picture of the body than either PET or CT alone. Typically, a PET image is color coded—different colors show various levels of cell activity. A CT scan shows the exact locations of the body's organs and also can show abnormal growths. When a CT scan is laid over a PET scan, a clinician or doctor can pinpoint the exact location of the PET-detected activity (e.g., tumoral FDG metabolism). They can also see the level and extent of that activity. Even when an abnormal growth is not yet visible on a CT scan, the PET scan can show the abnormal cell activity.

Further Chemotherapeutic Agents

In an embodiment of the invention, an IGF1R inhibitor is administered to a subject, in an method of the present invention, in association with erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR, KRX-0402, lucanthone, LY 317615, neuradiab, vitespan, Rta 744, Sdx 102, talampanel, atrasentan, Xr 311, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763 or AT-9263.

Abraxane is an injectable suspension of paclitaxel protein-bound particles comprising an albumin-bound form of paclitaxel with a mean particle size of approximately 130 nanometers. Abraxane is supplied as a white to yellow, sterile, lyophilized powder for reconstitution with 20 mL of 0.9% Sodium Chloride Injection, USP prior to intravenous infusion. Each single-use vial contains 100 mg of paclitaxel and approximately 900 mg of human albumin. Each milliliter (mL) of reconstituted suspension contains 5 mg paclitaxel. Abraxane is free of solvents and is free of cremophor (polyoxyethylated castor oil).

In an embodiment of the invention, an IGF1R inhibitor is administered to a subject, in an method of the present invention, in association with romidepsin (FK-228;

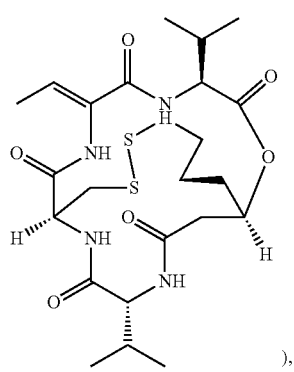
ADS-100380,
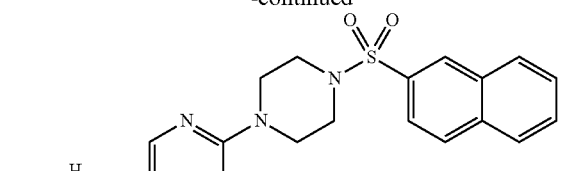
),
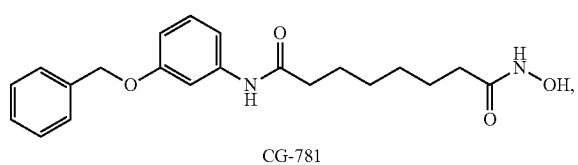
CG-781
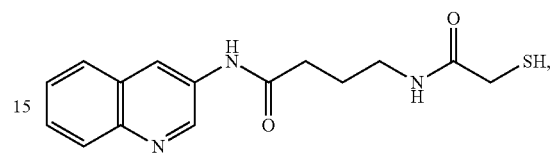
,
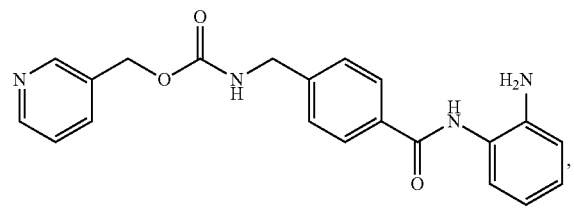
,
(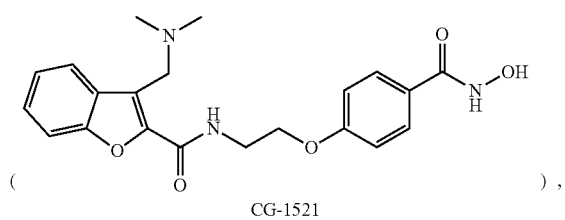),
CG-1521
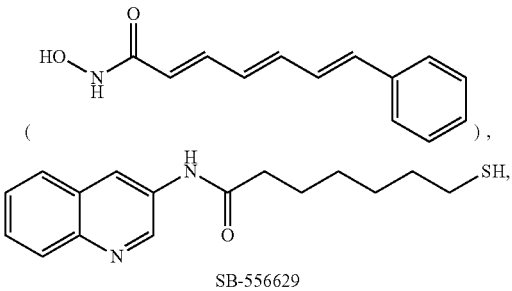,
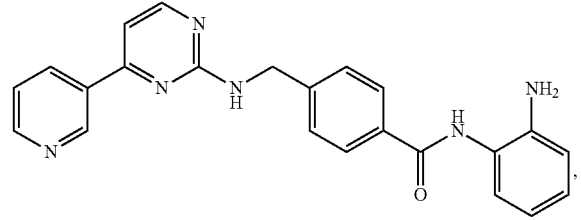
),
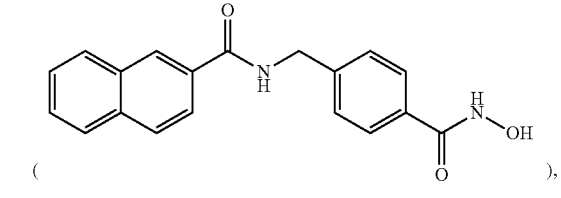
(),
SB-556629
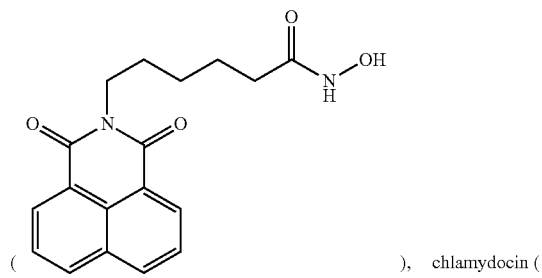
), chlamydocin (
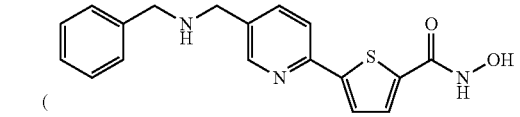
) or vorinostat (SAHA;
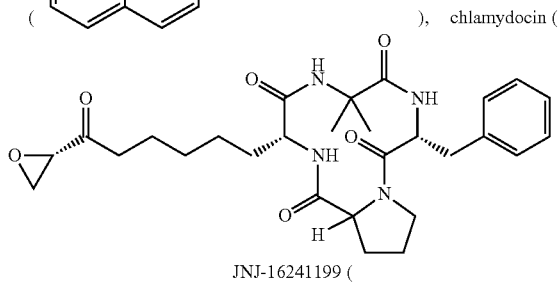
JNJ-16241199 (
(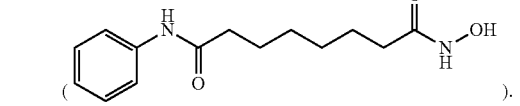).
In an embodiment of the invention, an IGF1R inhibitor is administered to a subject, in an method of the present invention, in association with etoposide (VP-16;

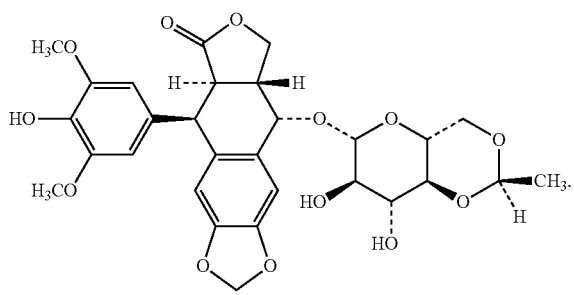

In an embodiment of the invention, an IGF1R inhibitor is administered to a subject, in an method of the present invention, in association with gemcitabine

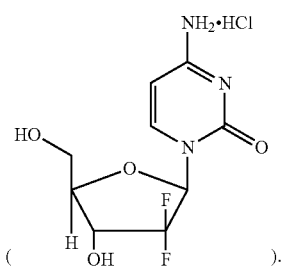

In an embodiment of the invention, an IGF1R inhibitor is administered to a subject, in an method of the present invention, in association with any compound disclosed in published U.S. patent application no. U.S. 2004/0209878A1 (e.g., comprising a core structure represented by

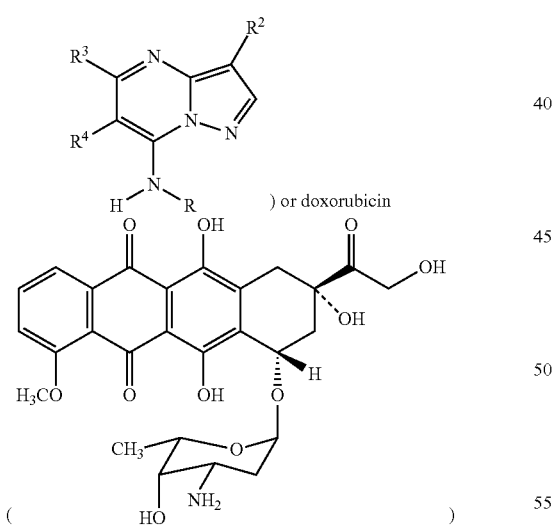

including Caelyx or Doxil® (doxorubicin HCl liposome injection; Ortho Biotech Products L.P; Raritan, N.J.). Doxil® comprises doxorubicin in STEALTH® liposome carriers which are composed of N-(carbonyl-methoxypolyethylene glycol 2000)-1,2-distearoyl-sn-glycero-3-phosphoethanolamine sodium salt (MPEG-DSPE); fully hydrogenated soy phosphatidylcholine (HSPC), and cholesterol.

In an embodiment of the invention, an IGF1R inhibitor is administered to a subject, in an method of the present invention, in association with 5'-deoxy-5-fluorouridine

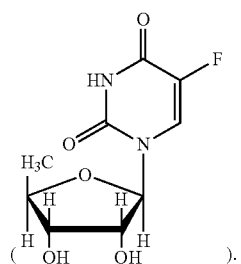

In an embodiment of the invention, an IGF1R inhibitor is administered to a subject, in an method of the present invention, in association with vincristine

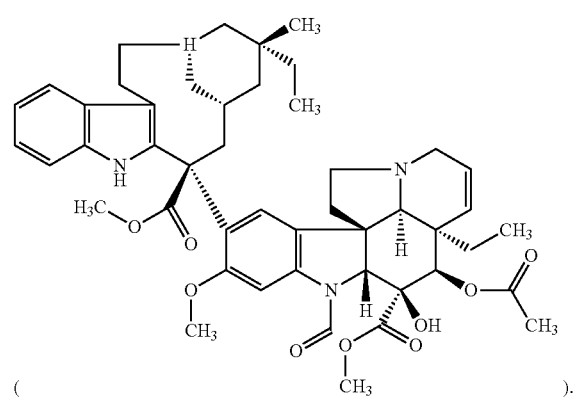

In an embodiment of the invention, an IGF1R inhibitor is administered to a subject, in an method of the present invention, in association with temozolomide

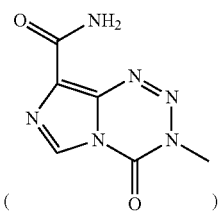

any CDK inhibitor such as ZK-304709, Seliciclib (R-roscovitine)

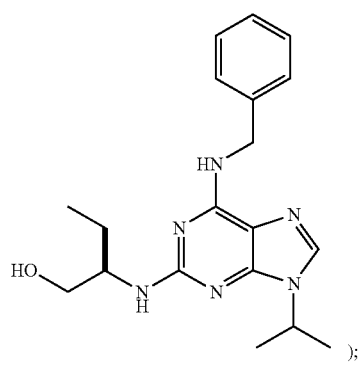 [SMILES: CC[C@H](CO)Nc1nc(NCc2ccccc2)c2ncn(C(C)C)c2n1]

any MEK inhibitor such as PD0325901

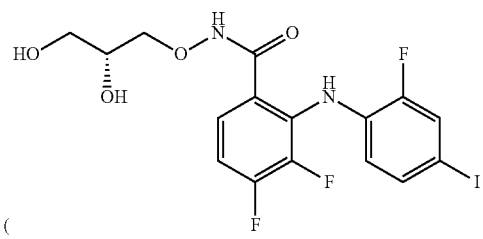

AZD-6244; capecitabine (5'-deoxy-5-fluoro-N-[(pentyloxy) carbonyl]-cytidine); or L-Glutamic acid, N-[4-[2-(2-amino-4,7-dihydro-4-oxo-1H-pyrrolo[2,3-d]pyrimidin-5-yl)ethyl] benzoyl]-, disodium salt, heptahydrate

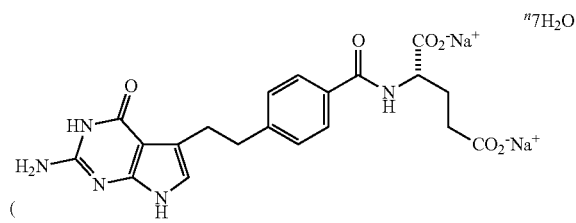

Pemetrexed disodium heptahydrate).

In an embodiment of the invention, an IGF1R inhibitor is administered to a subject, in an method of the present invention, in association with camptothecin

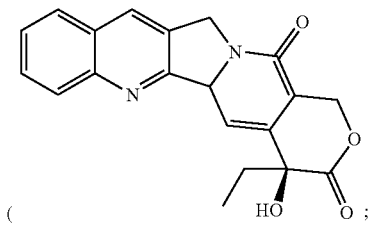

Stork et al., J. Am. Chem. Soc. 93(16): 4074-4075 (1971); Beisler et al., J. Med. Chem. 14(11): 1116-1117 (1962)), irinotecan

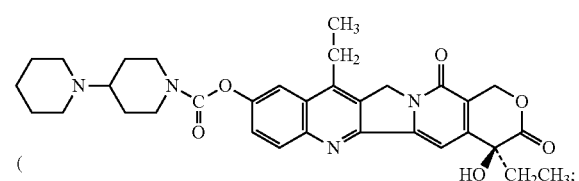

sold as Camptosar®; Pharmacia & Upjohn Co.; Kalamazoo, Mich.); a combination of irinotecan, 5-fluorouracil and leucovorin; or PEG-labeled irinotecan.

In an embodiment of the invention, an IGF1R inhibitor is administered to a subject, in an method of the present invention, in association with the FOLFOX regimen (oxaliplatin

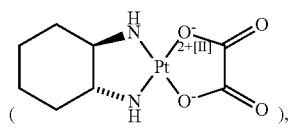

together with infusional fluorouracil

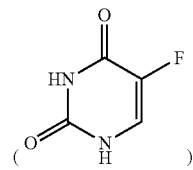

and folinic acid

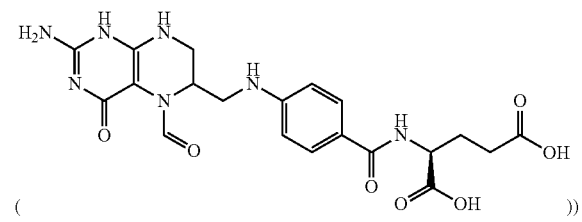

(Chaouche et al., Am. J. Clin. Oncol. 23(3):288-289 (2000); de Gramont et al., J. Clin. Oncol. 18(16):2938-2947 (2000)).

In an embodiment of the invention, an IGF1R inhibitor is administered to a subject, in an method of the present invention, in association with an antiestrogen such as

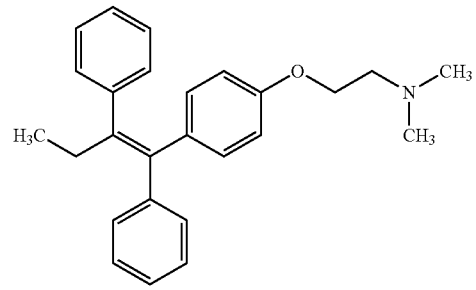 [SMILES: CC/C(=C(\c1ccccc1)c1ccc(OCCN(C)C)cc1)c1ccccc1]

(tamoxifen; sold as Nolvadex® by AstraZeneca Pharmaceuticals LP; Wilmington, Del.) or

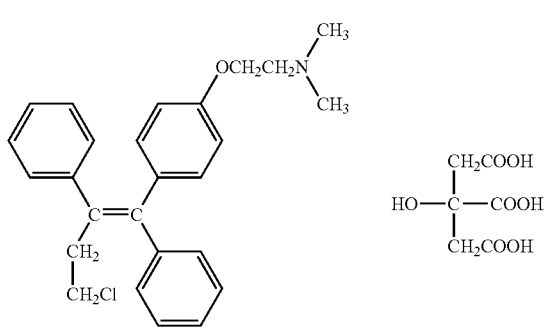

(toremifene citrate; sold as Fareston® by Shire US, Inc.; Florence, Ky.).

In an embodiment of the invention, an IGF1R inhibitor is administered to a subject, in an method of the present invention, in association with an aromatase inhibitor such as

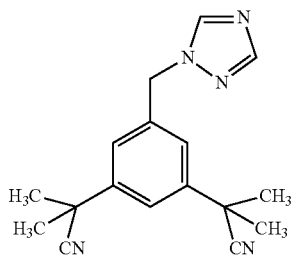 [SMILES: CC(C)(C#N)c1cc(Cn2cncn2)cc(C(C)(C)C#N)c1]

(anastrazole; sold as Arimidex® by AstraZeneca Pharmaceuticals LP; Wilmington, Del.),

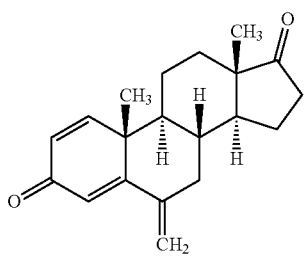

(exemestane; sold as Aromasin® by Pharmacia Corporation; Kalamazoo, Mich.) or

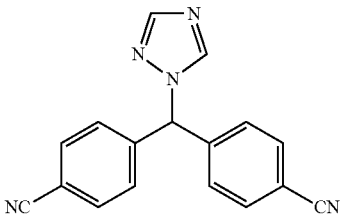 [SMILES: N#Cc1ccc(C(c2ccc(C#N)cc2)n2cncn2)cc1]

(letrozole; sold as Femara® by Novartis Pharmaceuticals Corporation; East Hanover, N.J.).

In an embodiment of the invention, an IGF1R inhibitor is administered to a subject, in an method of the present invention, in association with an estrogen such as DES (diethylstilbestrol),

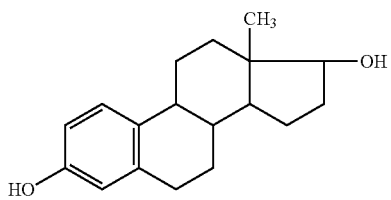 [SMILES: CC12CCC3c4ccc(O)cc4CCC3C1CCC2O]

(estradiol; sold as Estrol® by Warner Chilcott, Inc.; Rockaway, N.J.) or conjugated estrogens (sold as Premarin® by Wyeth Pharmaceuticals Inc.; Philadelphia, Pa.).

In an embodiment of the invention, an IGF1R inhibitor is administered to a subject, in an method of the present invention, in association with anti-angiogenesis agents including bevacizumab (Avastin™; Genentech; San Francisco, Calif.), the anti-VEGFR-2 antibody IMC-1C11, other VEGFR inhibitors such as: CHIR-258

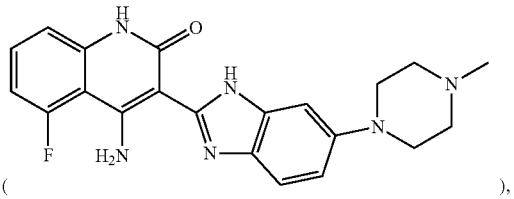

any of the inhibitors set forth in WO2004/13145 (e.g., comprising the core structural formula:

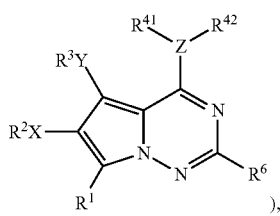

WO2004/09542 (e.g., comprising the core structural formula:

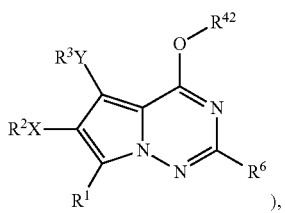

WO00/71129 (e.g., comprising the core structural formula:

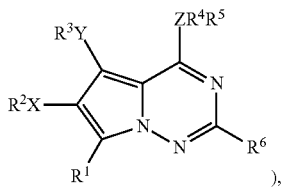

WO2004/09601 (e.g., comprising the core structural formula:

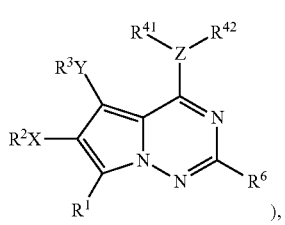

WO2004/01059 (e.g., comprising the core structural formula:

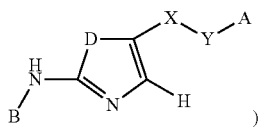
),

WO01/29025 (e.g., comprising the core structural formula:

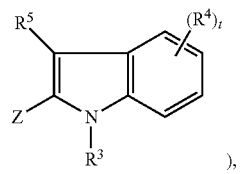
),

WO02/32861 (e.g., comprising the core structural formula:

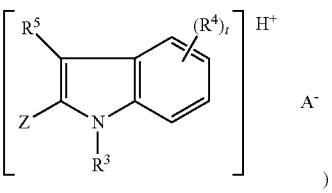
)

or set forth in WO03/88900 (e.g., comprising the core structural formula

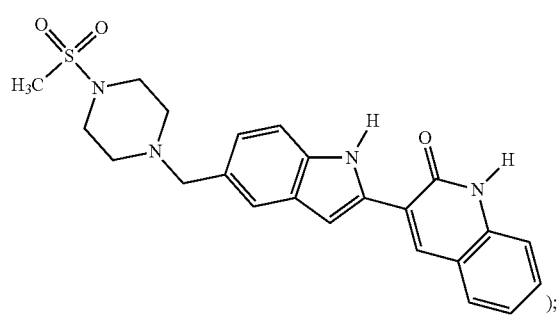 [SMILES: CS(=O)(=O)N1CCN(Cc2ccc3[nH]c(-c4cc5ccccc5[nH]c4=O)cc3c2)CC1]
);

3-[5-(methylsulfonylpiperadinemethyl)-indolyl]quinolone; Vatalanib

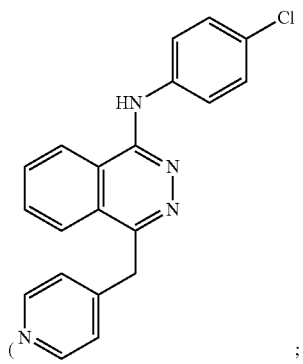
;

PTK/ZK; CPG-79787; ZK-222584), AG-013736

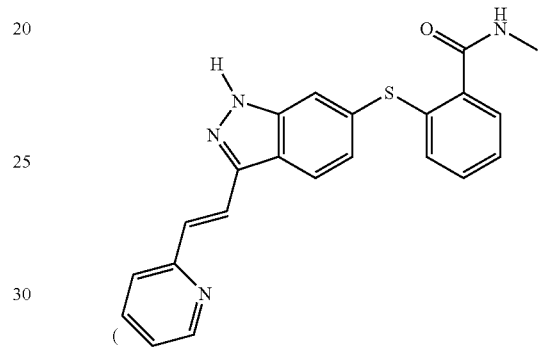
);

and the VEGF trap (AVE-0005), a soluble decoy receptor comprising portions of VEGF receptors 1 and 2.

In an embodiment of the invention, an IGF1R inhibitor is administered to a subject, in an method of the present invention, in association with a LHRH (Lutenizing hormone-releasing hormone) agonist such as the acetate salt of [D-Ser (Bu t) 6, Azgly 10](pyro-Glu-His-Trp-Ser-Tyr-D-Ser(Bu t)-Leu-Arg-Pro-Azgly-NH$_2$ acetate [C$_{59}$H$_{84}$N$_{18}$O$_{14}$·(C$_2$H$_4$O$_2$)$_x$ where x=1 to 2.4]; goserelin acetate (sold as Zoladex® by AstraZeneca UK Limited; Macclesfield, England), leuprolide acetate (sold as Eligard® by Sanofi-Synthelabo Inc.; New York, N.Y.) or triptorelin pamoate (sold as Trelstar® by Pharmacia Company, Kalamazoo, Mich.).

In an embodiment of the invention, an IGF1R inhibitor is administered to a subject, in an method of the present invention, in association with sunitinib or sunitinib malate

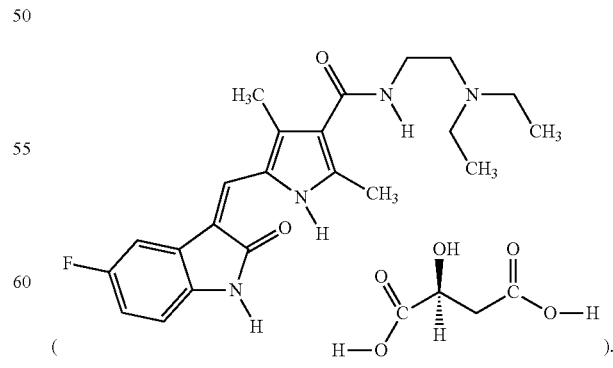
).

In an embodiment of the invention, an IGF1R inhibitor is administered to a subject, in an method of the present invention, in association with a progestational agent such as

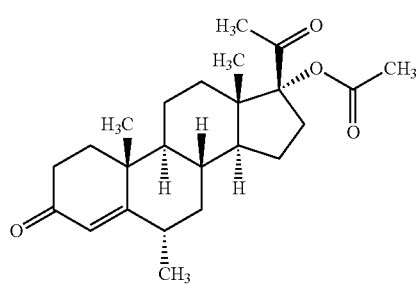

(medroxyprogesterone acetate; sold as Provera® by Pharmacia & Upjohn Co.; Kalamazoo, Mich.),

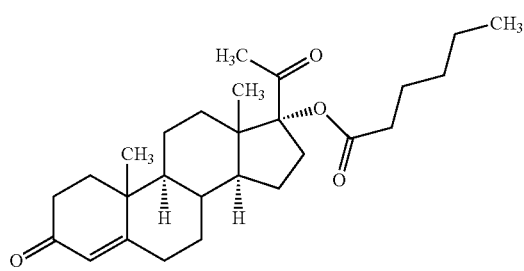

(hydroxyprogesterone caproate; 17-((1-Oxohexyl)oxy) pregn-4-ene-3,20-dione), megestrol acetate or progestins.

In an embodiment of the invention, an IGF1R inhibitor is provided in association with selective estrogen receptor modulator (SERM) such as

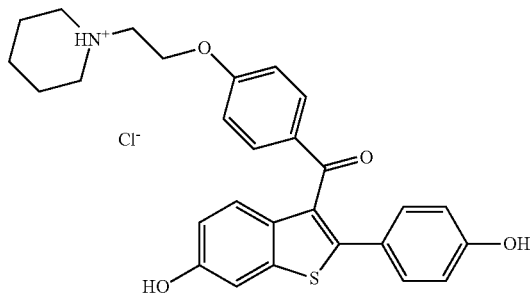

(raloxifene; sold as Evista® by Eli Lilly and Company; Indianapolis, Ind.).

In an embodiment of the invention, an IGF1R inhibitor is administered to a subject, in an method of the present invention, in association with an anti-androgen including, but not limited to:

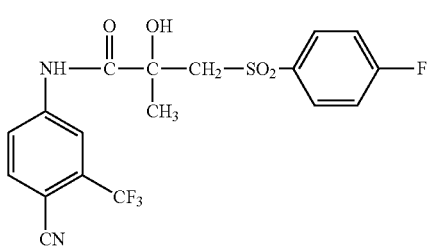 [SMILES: CC(O)(CS(=O)(=O)c1ccc(F)cc1)C(=O)Nc1ccc(C#N)c(C(F)(F)F)c1]

(bicalutamide; sold at CASODEX® by AstraZeneca Pharmaceuticals LP; Wilmington, Del.);

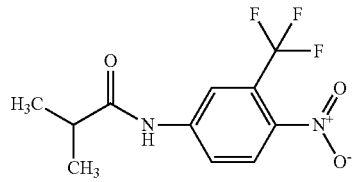

(flutamide; 2-methyl-N-[4-nitro-3 (trifluoromethyl)phenyl] propanamide; sold as Eulexin® by Schering Corporation; Kenilworth, N.J.);

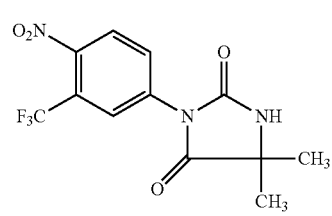 [SMILES: CC1(C)NC(=O)N(c2ccc([N+](=O)[O-])c(C(F)(F)F)c2)C1=O]

(nilutamide; sold as Nilandron® by Aventis Pharmaceuticals Inc.; Kansas City, Mo.) and

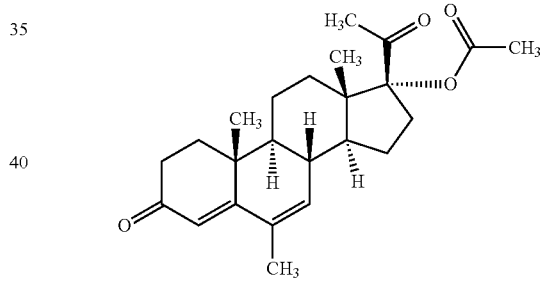

(Megestrol acetate; sold as Megace® by Bristol-Myers Squibb).

In an embodiment of the invention, an IGF1R inhibitor is administered to a subject, in an method of the present invention, in association with one or more inhibitors which antagonize the action of the EGF Receptor or HER2, including, but not limited to, CP-724714

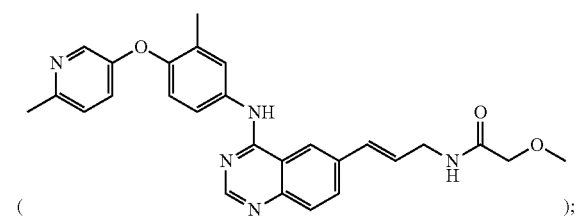

TAK-165

-continued

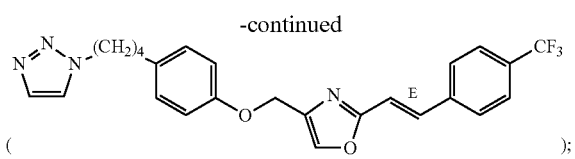

HKI-272

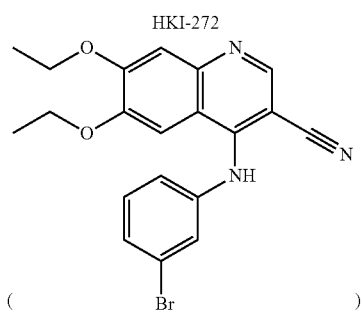

OSI-774 erlotinib, Hidalgo et al., J. Clin. Oncol. 19(13): 3267-3279 (2001)), Lapatanib

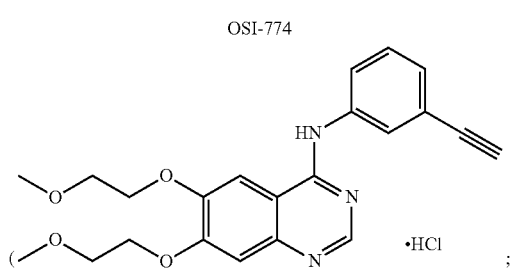

GW2016; Rusnak et al., Molecular Cancer Therapeutics 1:85-94 (2001); N-{3-Chloro-4-[(3-fluorobenzyl)oxy]phenyl}-6-[5-({[2-(methylsulfonyl)ethyl]amino}methyl)-2-furyl]-4-quinazolinamine; PCT Application No. WO99/35146), Canertinib (Cl-1033;

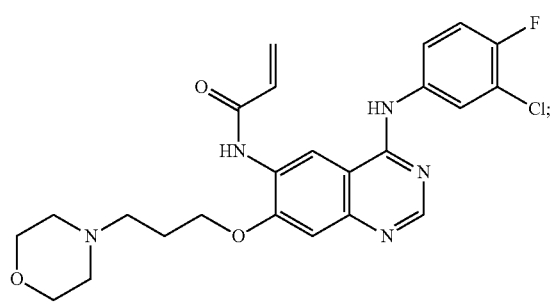 [SMILES: C=CC(=O)Nc1cc2c(Nc3ccc(F)c(Cl)c3)ncnc2cc1OCCCN1CCOCC1]

Erlichman et al., Cancer Res. 61(2):739-48 (2001); Smaill et al., J. Med. Chem. 43(7):1380-97 (2000)), ABX-EGF antibody (Abgenix, Inc.; Freemont, Calif.; Yang et al., Cancer Res. 59(6):1236-43 (1999); Yang et al., Crit. Rev Oncol Hematol. 38(1):17-23 (2001)), erbitux (U.S. Pat. No. 6,217,866; IMC-C225, cetuximab; Imclone; New York, N.Y.), EKB-569

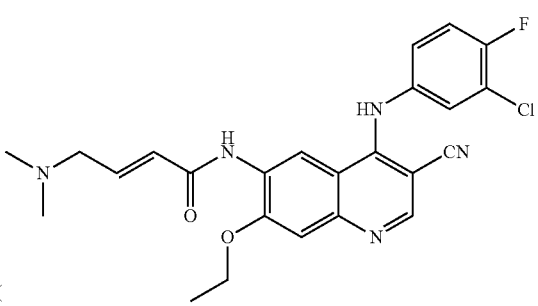

Wissner et al., J. Med. Chem. 46(1): 49-63 (2003)), PKI-166

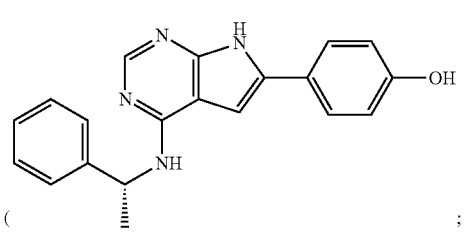

CGP-75166), GW-572016, any anti-EGFR antibody and any anti-HER2 antibody.

In an embodiment of the invention, an IGF1R inhibitor is administered to a subject, in an method of the present invention, in association with:

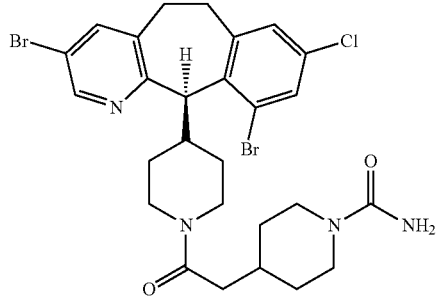

(lonafarnib; Sarasar™; Schering-Plough; Kenilworth, N.J.). In another embodiment, an IGF1R inhibitor is administered to a subject, in an method of the present invention, in association with one or more FPT inhibitors such as:

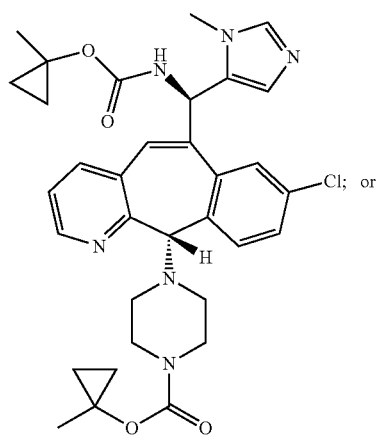

Other FPT inhibitors include BMS-214662

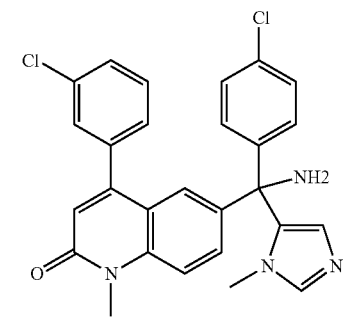 [SMILES: Cn1cncc1C(N)(c1ccc(Cl)cc1)c1ccc2c(c1)c(-c1cccc(Cl)c1)cc(=O)n2C]

Hunt et al., J. Med. Chem. 43(20):3587-95 (2000); Dancey et al., Curr. Pharm. Des. 8:2259-2267 (2002); (R)-7-cyano-2,3,4,5-tetrahydro-1-(1H-imidazol-4-ylmethyl)-3-(phenylmethyl)-4-(2-thienylsulfonyl)-1H-1,4-benzodiazepine)) and R155777 (tipifarnib; Garner et al., Drug Metab. Dispos. 30(7):823-30 (2002); Dancey et al., Curr. Pharm. Des. 8:2259-2267 (2002); (B)-6-[amino(4-chlorophenyl)(1-methyl-1H-imidazol-5-yl)-methyl]-4-(3-chlorophenyl)-1-methyl-2(1H)-quinolinone];

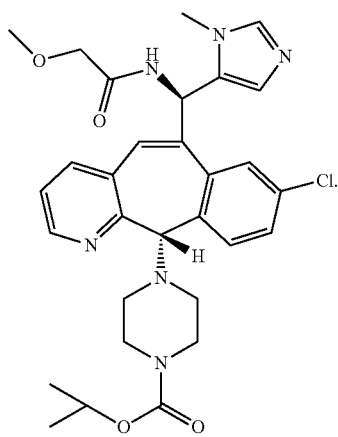

sold as Zarnestra™; Johnson & Johnson; New Brunswick, N.J.).

In an embodiment of the invention, an IGF1R inhibitor is administered to a subject, in an method of the present invention, in association with

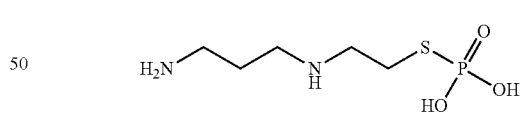

(Amifostine);

(NVP-LAQ824; Atadja et al., Cancer Research 64: 689-695 (2004)),

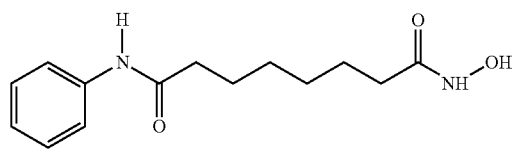 [SMILES: O=C(CCCCCCC(=O)Nc1ccccc1)NO]
(suberoyl analide hydroxamic acid),
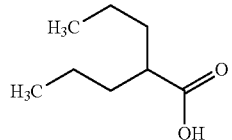
(Valproic acid; Michaelis et al., Mol. Pharmacol. 65:520-527 (2004)),
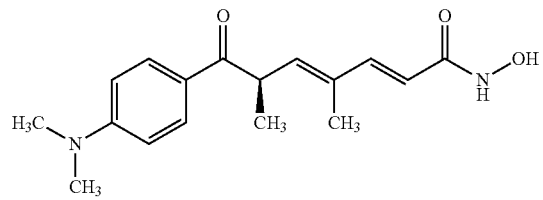 [SMILES: CC(/C=C/C(=O)NO)=C\[C@@H](C)C(=O)c1ccc(N(C)C)cc1]
(trichostatin A),
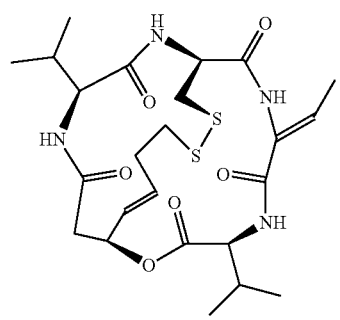
(FK-228; Furumai et al., Cancer Research 62: 4916-4921 (2002)),
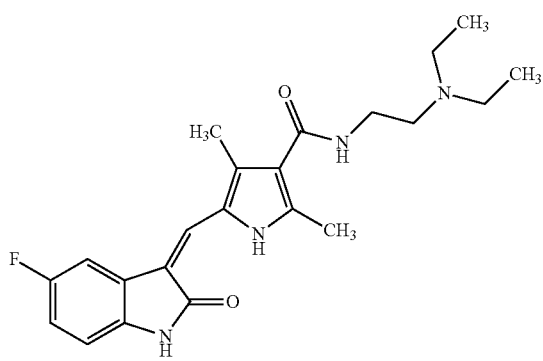 [SMILES: CCN(CC)CCNC(=O)c1c(C)[nH]c(/C=C2\C(=O)Nc3ccc(F)cc32)c1C]
(SU11248; Mendel et al., Clin. Cancer Res. 9(1):327-37 (2003)),
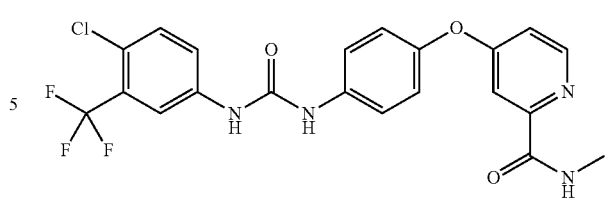
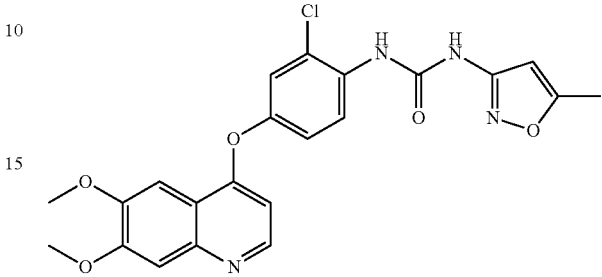
(BAY43-9006; sorafenib),
(KRN951),
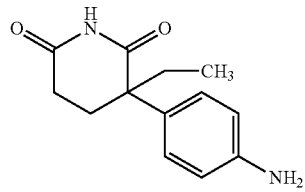
(Aminoglutethimide);
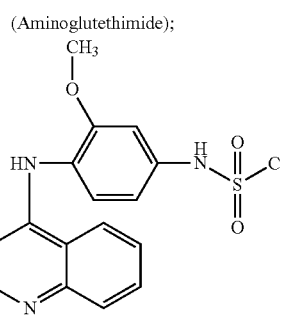
(Amsacrine);
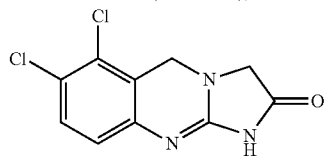
(Anagrelide);
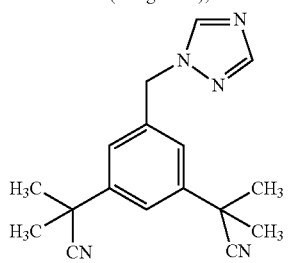
(Anastrozole;

sold as Arimidex by AstraZeneca Pharmaceuticals LP; Wilmington, Del.); Asparaginase; Bacillus Calmette-Guerin (BCG) vaccine (Garrido et al, Cytobios. 90(360):47-65 (1997));

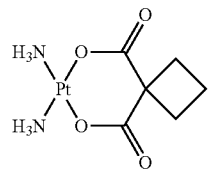

(Carboplatin; sold as Paraplatin® by Bristol-Myers Squibb; Princeton, N.J.);

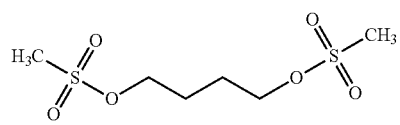

(Busulfan; 1,4-butanediol, dimethanesulfonate; sold as Busulfex® by ESP Pharma, Inc.; Edison, New Jersey);

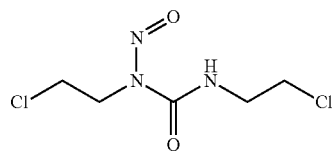 [SMILES: O=NN(CCCl)C(=O)NCCCl]

(Carmustine);

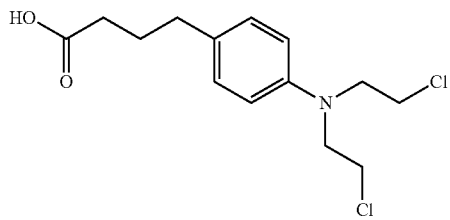

(Chlorambucil)

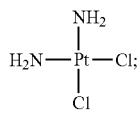

(Cisplatin)

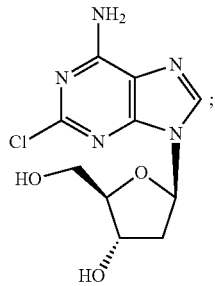

(Cladribine)

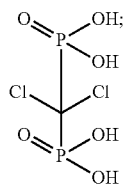

(Clodronate)

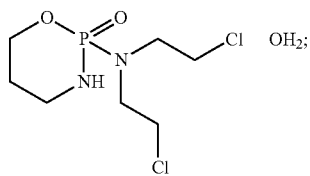

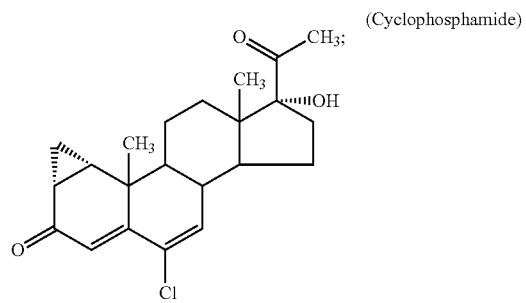
(Cyclophosphamide)
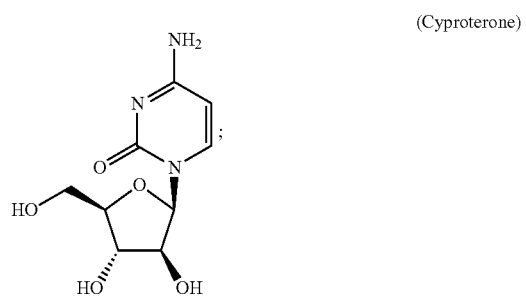
(Cyproterone)
(Cytarabine)
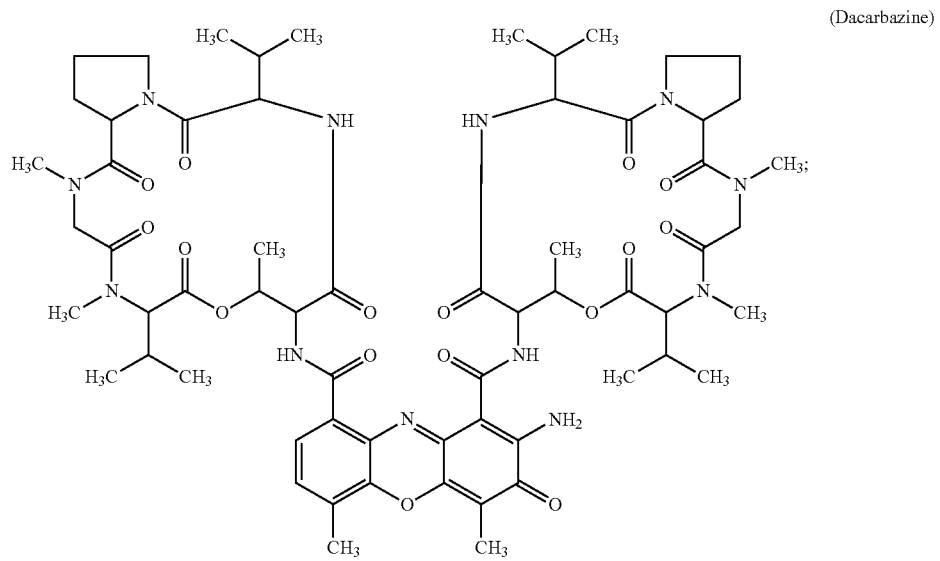
(Dacarbazine)

-continued
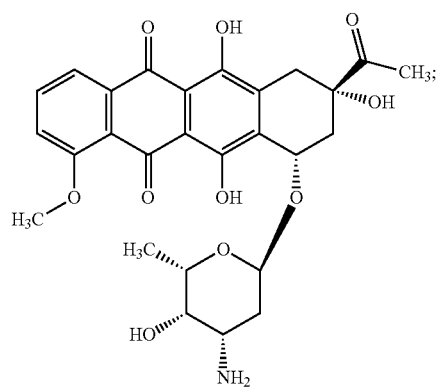
(Dactinomycin)
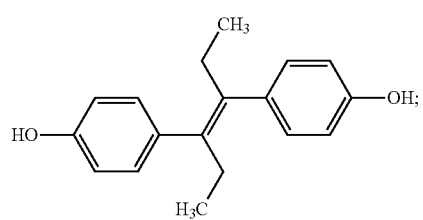
(Daunorubincin)
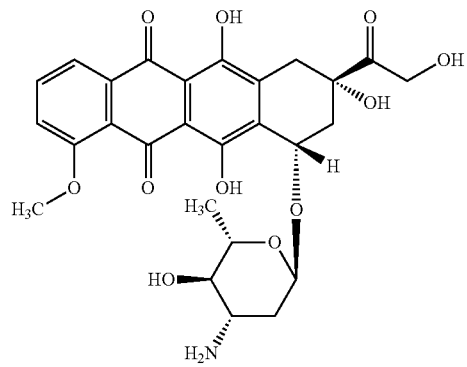
(Diethylstilbestrol)
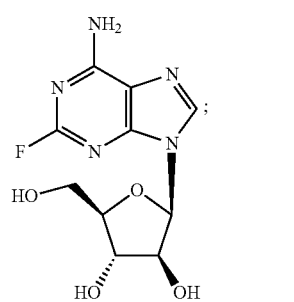
(Epirubicin)
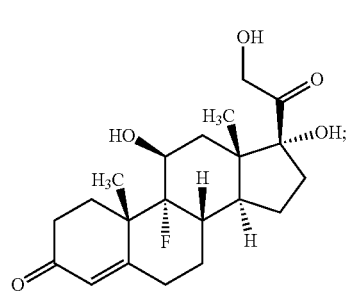
(Fludarabine)

-continued
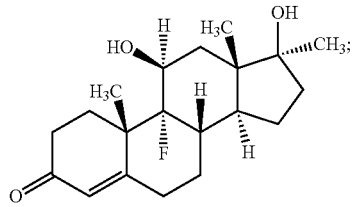
(Fludrocortisone)
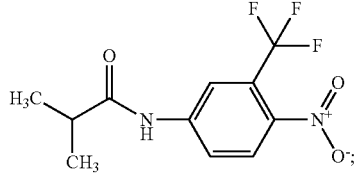
(Fluoxymesterone)
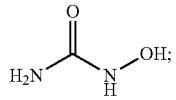
(Flutamide)
(Hydroxyurea)
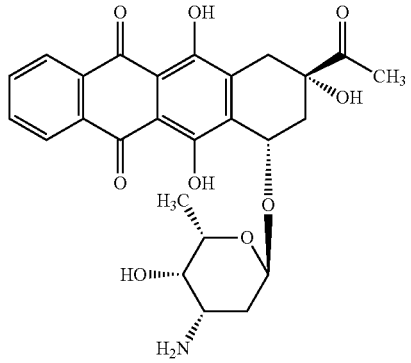
(Idarubicin)
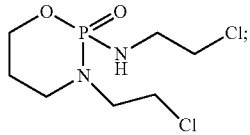
(Ifosfamide)
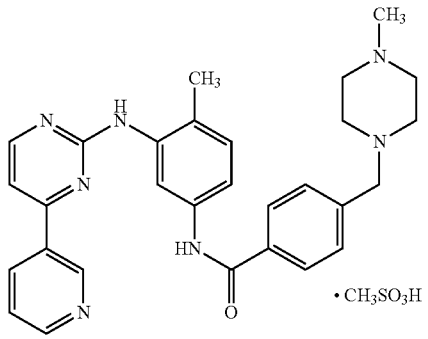

41
(Imatinib; sold as Gleevec® by Novartis Pharmaceuticals Corporation; East Hanover, N.J.);
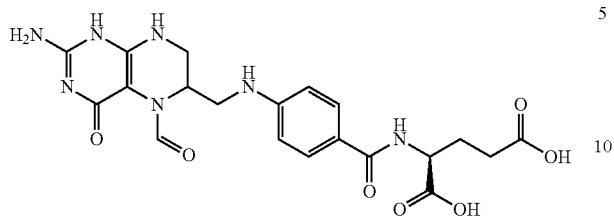
(Leucovorin);
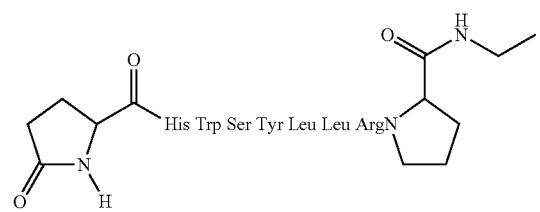
(Leuprolide);
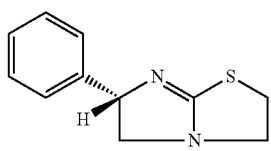
(Levamisole);
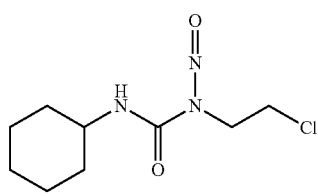 [SMILES: O=NN(CCCl)C(=O)NC1CCCCC1]
(Lomustine);
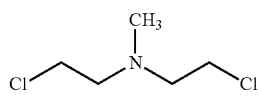
(Mechlorethamine);
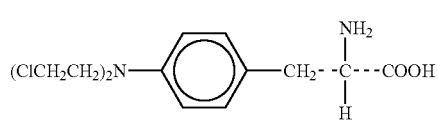
42
(Melphalan; sold as Alkeran® by Celgene Corporation; Warren, N.J.);
(Mercaptopurine)
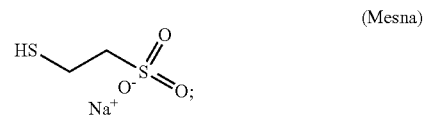
(Mesna)
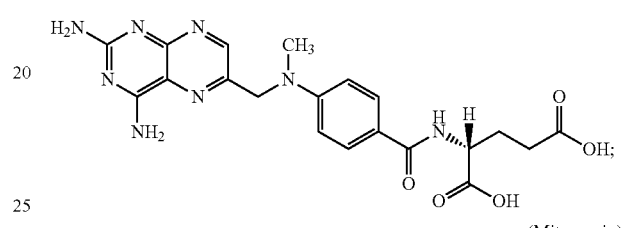
(Methotrexate)
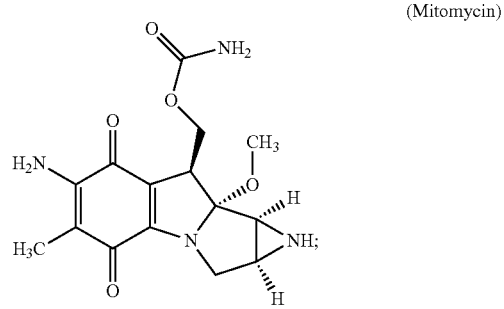
(Mitomycin)
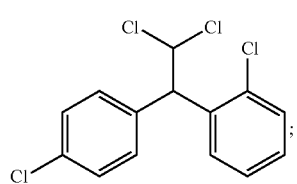
(Mitotane)
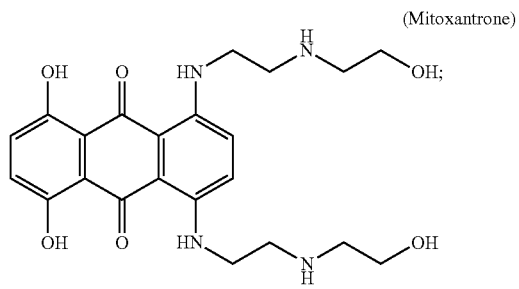
(Mitoxantrone)
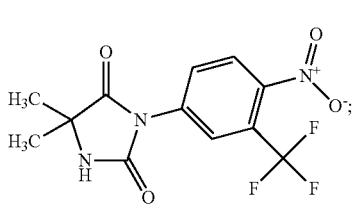
(Nilutamide)

octreotide (

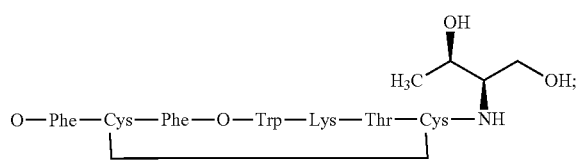

Katz et al., Clin Pharm. 8(4):255-73 (1989); sold as Sandostatin LAR® Depot; Novartis Pharm. Corp; E. Hanover, N.J.); edotreotide (yttrium-90 labeled or unlabeled); oxaliplatin

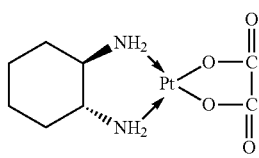

sold as Eloxatin™ by Sanofi-Synthelabo Inc.; New York, N.Y.);

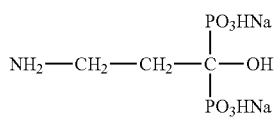

(Pamidronate; sold as Aredia® by Novartis Pharmaceuticals Corporation; East Hanover, N.J.);

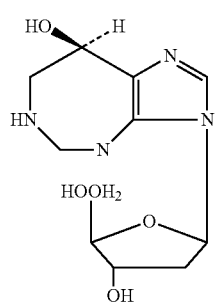

(Pentostatin; sold as Nipent® by Supergen; Dublin, Calif.); Plicamycin; Porfimer (sold as Photofrin® by Axcan Scandipharm Inc.; Birmingham, Ala.);

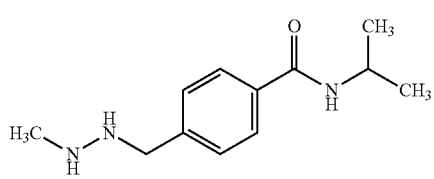 [SMILES: CNNCc1ccc(C(=O)NC(C)C)cc1]

(Procarbazine);

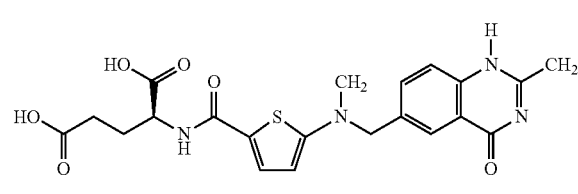 [SMILES: Cc1nc(=O)c2cc(CN(C)c3ccc(C(=O)N[C@@H](CCC(=O)O)C(=O)O)s3)ccc2[nH]1]

(Raltitrexed); Rituximab (sold as Rituxan® by Genentech, Inc.; South San Francisco, Calif.);

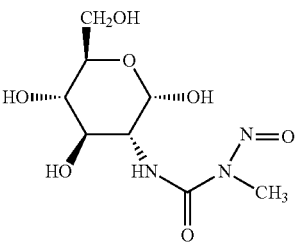 [SMILES: CN(N=O)C(=O)N[C@@H]1[C@@H](O)[C@H](O)[C@@H](CO)O[C@@H]1O]

(Streptozocin);

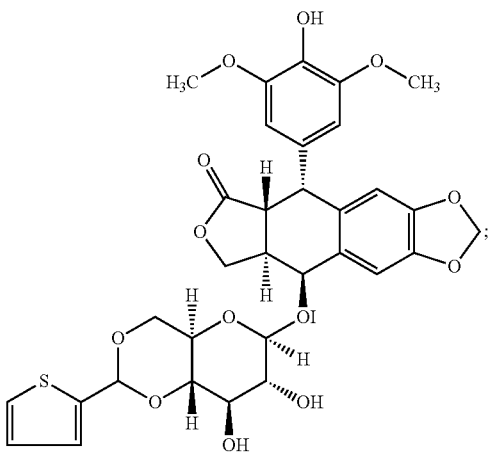

(Teniposide)

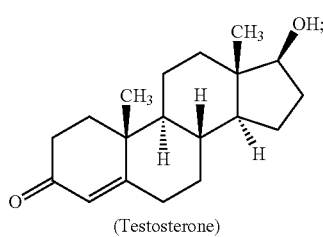

(Testosterone)

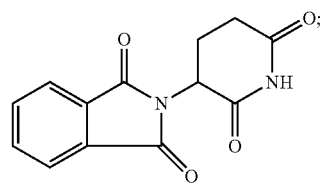

(Thalidomide)

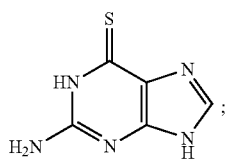

(Thioguanine)

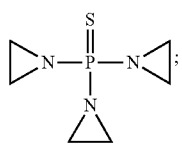

(Thiotepa)

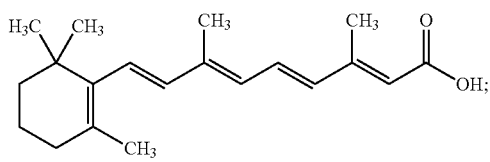

(Tretinoin)

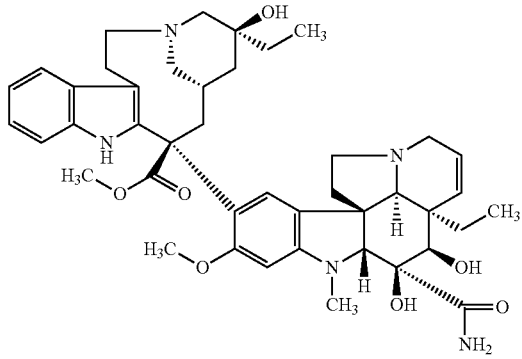

(Vindesine) or 13-cis-retinoic acid

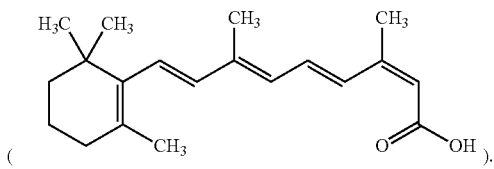

In an embodiment of the invention, an IGF1R inhibitor is administered to a subject, in an method of the present invention, in association with one or more of any of: phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin, diftitox, gefitinib, bortezimib, paclitaxel, docetaxel, epithilone B, BMS-247550 (see e.g., Lee et al., Clin. Cancer Res. 7:1429-1437 (2001)), BMS-310705, droloxifene (3-hydroxytamoxifen), 4-hydroxytamoxifen, pipendoxifene, ERA-923, arzoxifene, fulvestrant, acolbifene, lasofoxifene (CP-336156), idoxifene, TSE-424, HMR-3339, ZK186619, topotecan, PTK787/ZK 222584 (Thomas et al., Semin Oncol. 30(3 Suppl 6):32-8 (2003)), the humanized anti-VEGF antibody Bevacizumab, VX-745 (Haddad, Curr Opin. Investig. Drugs 2(8):1070-6 (2001)), PD 184352 (Sebolt-Leopold, et al. Nature Med. 5: 810-816 (1999)), any mTOR inhibitor, rapamycin

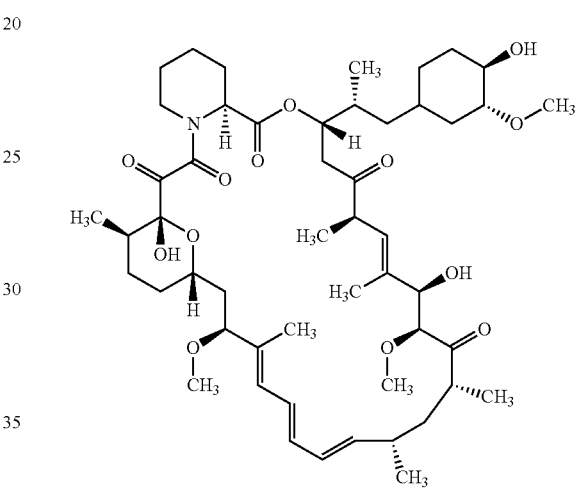

sirolimus), 40-O-(2-hydroxyethyl)-rapamycin, CCI-779

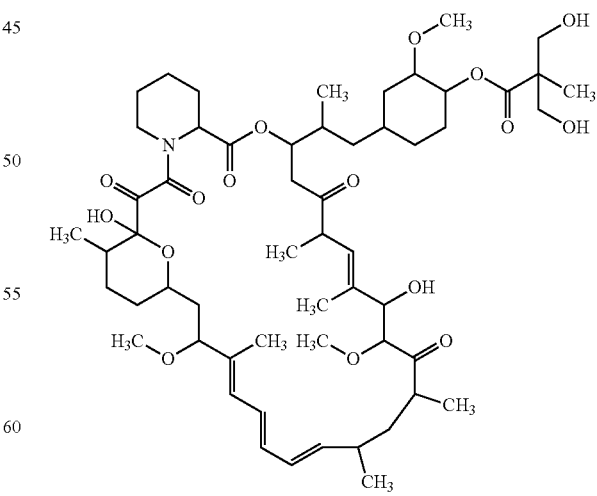

(temsirolimus; Sehgal et al., Med. Res. Rev., 14:1-22 (1994); Elit, Curr. Opin. Investig. Drugs 3(8):1249-53 (2002)), AP-23573

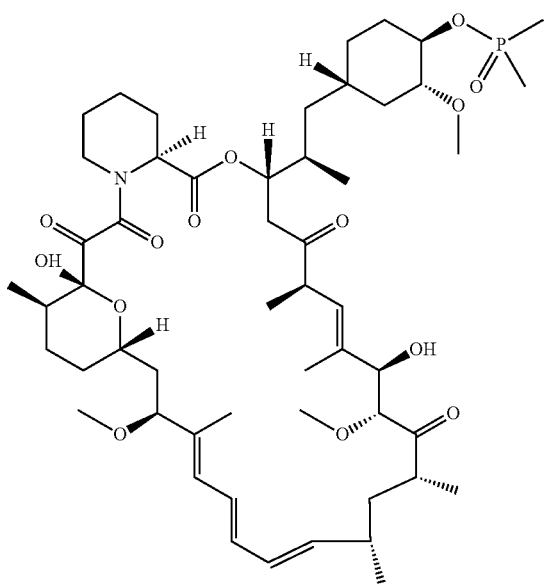

RAD001 ( )

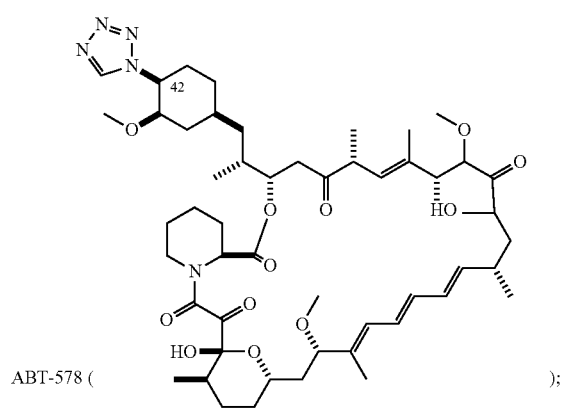

ABT-578 ( );

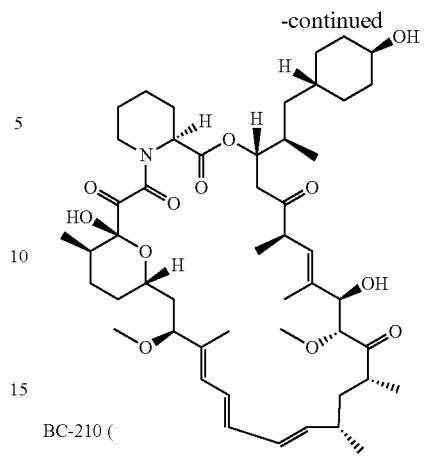

BC-210 ( ),

LY294002, LY292223, LY292696, LY293684, LY293646 (Viahos et al., J. Biol. Chem. 269(7): 5241-5248 (1994)), wortmannin, BAY-43-9006, (Wilhelm et al., Curr. Pharm. Des. 8:2255-2257 (2002)), ZM336372, L-779,450, any Raf inhibitor disclosed in Lowinger et al., Curr. Pharm Des. 8:2269-2278 (2002); flavopiridol (L86-8275/HMR 1275; Senderowicz, Oncogene 19(56): 6600-6606 (2000)) or UCN-01 (7-hydroxy staurosporine; Senderowicz, Oncogene 19(56): 6600-6606 (2000)).

In an embodiment of the invention, an IGF1R inhibitor is administered to a subject, in an method of the present invention, in association with one or more of any of the compounds set forth in U.S. Pat. No. 5,656,655, which discloses styryl substituted heteroaryl EGFR inhibitors; in U.S. Pat. No. 5,646,153 which discloses bis mono and/or bicyclic aryl heteroaryl carbocyclic and heterocarbocyclic EGFR and PDGFR inhibitors; in U.S. Pat. No. 5,679,683 which discloses tricyclic pyrimidine compounds that inhibit the EGFR; in U.S. Pat. No. 5,616,582 which discloses quinazoline derivatives that have receptor tyrosine kinase inhibitory activity; in Fry et al., Science 265 1093-1095 (1994) which discloses a compound having a structure that inhibits EGFR (see FIG. 1 of Fry et al.); in U.S. Pat. No. 5,196,446 which discloses heteroarylethenediyl or heteroarylethenediylaryl compounds that inhibit EGFR; in Panek, et al., Journal of Pharmacology and Experimental Therapeutics 283: 1433-1444 (1997) which disclose a compound identified as PD166285 that inhibits the EGFR, PDGFR, and FGFR families of receptors-PD166285 is identified as 6-(2,6-dichlorophenyl)-2-(4-(2-diethylaminoethoxy)phenylamino)-8-methyl-8H-pyrido (2,3-d)pyrimidin-7-one.

In an embodiment of the invention, an IGF1R inhibitor is provided in association with one or more of any of: pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3 and pegylated, unpegylated consensus interferon or albumin-interferon-alpha.

Other interferon alpha conjugates can be prepared by coupling an interferon alpha to a water-soluble polymer. A non-limiting list of such polymers includes other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described, for example, in U.S. Pat. No. 4,766,106, U.S. Pat. No. 4,917,888, European Patent Application No. 0 236 987 or 0 593 868 or International Publication No. WO 95/13090.

The scope of the present invention also includes methods wherein an IGF1R inhibitor is administered to a subject in association with one or more antiemetics including, but not limited to, casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, NC), granisetron (sold as Kytril® by Hoffmann-La Roche Inc.; Nutley, N.J.), ondansetron (sold as Zofran® by by Glaxosmithkline; Research Triangle Park, NC), dolasetron (sold as Anzemet® by Sanofi-Aventis; New York, N.Y.), tropisetron (sold as Navoban® by Novartis; East Hanover, N.J.).

The present invention also includes methods for treating or preventing Ewing's sarcoma in a subject by administering an IGF1R inhibitor optionally in association with one or more other chemotherapeutic agents (e.g., as described herein) and/or optionally in association with one or more antiemetics.

Other side effects of cancer treatment include red and white blood cell deficiency. Accordingly, the present invention includes compositions comprising an IGF1R inhibitor optionally in association with an agent which treats or prevents such a deficiency, such as, e.g., pegfilgrastim, erythropoietin, epoetin alfa or darbepoetin alfa.

The present invention further comprises a method for treating or preventing any stage or type of any medical condition set forth herein by administering an IGF1R inhibitor in association with a therapeutic procedure such as surgical tumorectomy or anti-cancer radiation treatment; optionally in association with a further chemotherapeutic agent and/or antiemetic, for example, as set forth above.

The term "in association with" indicates that the components administered in a method of the present invention (e.g., anti-IGF1R antibody or antigen-binding fragment thereof along with imatinib) can be formulated into a single composition for simultaneous delivery or formulated separately into two or more compositions (e.g., a kit). Furthermore, each component can be administered to a subject at a different time than when the other component is administered; for example, each administration may be given non-simultaneously (e.g., separately or sequentially) at several intervals over a given period of time. Moreover, the separate components may be administered to a subject by the same or by a different route (e.g., wherein an anti-IGF1R antibody is administered parenterally and gosrelin acetate is administered orally).

In addition, the present invention includes embodiments wherein the subject receives an IGF1R inhibitor (e.g., as discussed herein) along with a multidrug chemotherapy comprising vincristine, doxorubicin, ifosfamide, and etoposide and, optionally, cyclophosphamide and/or dactinomycin. In an embodiment of the invention, the subject receives an IGF1R inhibitor (e.g., as discussed herein) along with a multidrug chemotherapy comprising alternating courses of vincristine, cyclophosphamide, and doxorubicin with courses of ifosfamide/etoposide. In an embodiment of the invention, the subject receives an IGF1R inhibitor (e.g., as discussed herein) along with a multidrug chemotherapy comprising vincristine, doxorubicin, and an alkylating agent with or without etoposide, e.g., in a single treatment cycle.

Therapeutic Methods, Formulations, Dosage and Administration

The present invention provides methods for PET imaging a tumor in a subject receiving and/or about to receive IGF1R inhibitor therapy. In an embodiment of the invention, the subject suffers from Ewing's sarcoma, e.g., recurrent or relapsed Ewing's sarcoma wherein the subject has failed to respond any further to frontline therapies.

The term "subject" or "patient" refers to a mammal such as a human (e.g., a human adult or child) or a mouse, rat, rabbit, dog or other canine, horse, goat or primate such as a monkey, chimpanzee or gorilla.

For example, the present invention includes a method for treating a Ewing's sarcoma tumor, in a subject, comprising evaluating glucose metabolism of the tumor after the subject has received a first dose of IGF1R inhibitor, but before a second dose of the inhibitor; or within about 14 days of a first dose of IGF1R inhibitor but before a second dose of said inhibitor; wherein treatment with the IGF1R inhibitor is discontinued if glucose metabolism does not significantly decrease or remain constant after said first dose; and continuing treatment with the IGF1R inhibitor if glucose metabolism does significantly decrease or remain constant after said first dose. Optionally, if the inhibitor does not exhibit sufficient efficacy, the dose can be increased, followed by a reevaluation of the tumor glucose metabolism relative the tumor glucose metabolism before the increased dose and, e.g., a determination as to whether to continue treatment, discontinue treatment or increase dosage as discussed above.

The present invention also includes a method for evaluating the effect of an IGF1R inhibitor on a Ewing's sarcoma tumor, in a subject, comprising evaluating glucose metabolism of the tumor after the subject has received a first dose of IGF1R inhibitor, but before a second dose of the inhibitor; or within 14 days of a first dose of IGF1R inhibitor but before a second dose of said inhibitor; wherein the inhibitor is determined not to exhibit sufficient efficacy against the tumor if glucose metabolism does not significantly decrease or remain constant after said first dose; and determining that the inhibitor does exhibit sufficient efficacy if glucose metabolism does significantly decrease or remain constant after said first dose. Optionally, if the inhibitor exhibits sufficient efficacy, treatment can be continued; or if the inhibitor does not exhibit sufficient efficacy, the treatment can be discontinued or the dose can be increased, followed by a reevaluation of the tumor glucose metabolism relative the tumor glucose metabolism before the increased dose, and, e.g., a determination as to whether to continue treatment, discontinue treatment or increase dosage as discussed above.

The IGF1R inhibitors discussed herein (e.g., anti-IGF1R antibodies and antigen-binding fragments thereof) and compositions thereof are, in an embodiment of the invention, administered at a therapeutically effective dosage. The term "therapeutically effective amount" or "therapeutically effective dosage" means that amount or dosage of an IGF1R inhibitor or composition thereof that will elicit a biological or medical response of a tissue, system, patient, subject or host that is being sought by the administrator (such as a researcher, doctor or veterinarian) which includes any measurable alleviation of the signs, symptoms and/or clinical indicia of a medical disorder, such as cancer (e.g., tumor growth and/or metastasis) including the prevention, slowing or halting of progression of the medical disorder to any degree whatsoever. For example, in one embodiment of the invention, a "therapeutically effective dosage" of any anti-IGF1R antibody or antigen-binding fragment thereof discussed herein (e.g., an anti-IGF1R antibody comprising mature LCC, LCD, LCE or LCF light chain and/or mature HCA or HCB heavy chain) is between about 0.3 and 20 mg/kg of body weight (e.g., about 0.3 mg/kg of body weight, about 0.6 mg/kg of body weight, about 0.9 mg/kg of body weight, about 1 mg/kg of body weight, about 2 mg/kg of body weight, about 3 mg/kg of body weight, about 4 mg/kg of body weight, about 5 mg/kg of body weight, about 6 mg/kg of body weight, about 7 mg/kg of body weight, about 8 mg/kg of body weight, about 9 mg/kg of body weight, about 10 mg/kg of body weight, about 11 mg/kg of body weight, about 12 mg/kg of body weight, about 13 mg/kg of body weight, about 14 mg/kg of body weight, about 15 mg/kg of body weight, about 16 mg/kg of body weight, about 17 mg/kg of body weight, about 18 mg/kg of body weight, about 19 mg/kg of body weight, about 20 mg/kg of body weight), e.g., about once per week to about once every 3 weeks (e.g., about once every 1 week or once every 2 weeks or once every 3 weeks). The therapeutically effective dosage of an IGF1R inhibitor or any further therapeutic agent is, when possible, as set forth in *Physicians Desk Reference* 2010; Thomson Reuters; 64 edition (Nov. 15, 2009); and/or in *Physicians' Desk Reference* 2009; Thomson Reuters; 63rd edition (Nov. 30, 2008) or in the prescribing information of the relevant drug label (if available), such as the US FDA drug label.

The present invention includes methods for using a pharmaceutical composition comprising an IGF1R inhibitor. The pharmaceutical compositions may be prepared by any methods well known in the art of pharmacy; see, e.g., Gilman, et al., (eds.) (1990), *The Pharmacological Bases of Therapeutics,* 8th Ed., Pergamon Press; A. Gennaro (ed.), *Remington's Pharmaceutical Sciences,* 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

A pharmaceutical composition containing an IGF1R inhibitor can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like. All routes of administration are contemplated including, but not limited to, parenteral (e.g., subcutaneous, intratumoral, intravenous, intraperitoneal, intramuscular) and non-parenteral (e.g., oral, transdermal, intranasal, intraocular, sublingual, inhalation, rectal and topical). In an embodiment of the invention, the anti-IGF1R antibody comprises about 20 mg/ml of the antibody, water, about 70 mg/ml sucrose, about 2.3 mg/ml sodium acetate trihydrate, and about 0.08 mg/ml glacial acetic acid, at a pH of about 5.5.

Injectables can be prepared in conventional forms, either as liquid solutions or suspensions, solid forms suitable for solution or suspension in liquid prior to injection, or as emulsions. The injectables, solutions and emulsions can also contain one or more excipients. Excipients are, for example, water, sugar, buffer, salt, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

In an embodiment, pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN-80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

In an embodiment of the invention, preparations for parenteral administration can include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

EXAMPLES

The present invention is intended to exemplify the present invention and not to be a limitation thereof. Method disclosed below fall within the scope of the present invention. Methods of the present invention may be modified by any one or more of the parameters set forth in the example below.

Example 1

Correlation of FDG-PET Signal to Anti-IGF1R Efficacy

The present study of FDG-PET signals in subjects receiving anti-IGF1R therapy is ongoing. These data represent that which is available at the time of filing. These data demonstrated that, when evaluated early in the treatment regimen (within 7-14 days of initial dose of anti-IGF1R), a decrease in $^{18}$F-fluorodeoxyglucose metabolism, as measured via single FDG-PET scan, is a valuable predictor of antibody efficacy.

Seventy one subjects with Ewing's sarcoma (relapsed or recurrent) were enrolled on a clinical protocol for treatment with anti-IGF1R (comprising the light chain variable domain comprising amino acids 20-128 (linked to a kappa constant domain) and the heavy chain variable domain comprising amino acid 20-137 of SEQ ID NO: 10 (linked to a gamma-1 constant domain)). 66 were potentially evaluable, and some of these subjects were without PET scan data. Subjects have been followed for up to 30 weeks. In the Ewing's sarcoma group, 66 potentially evaluable patients have completed at least 4 doses (10 mg/kg every two weeks). Tumor regressions or tumor response to treatment have been observed and reported in at least subjects in the form of partial responses. Stable disease has been observed in 4 or more subjects (decreasing or stable tumor burden but not sufficient for response). Of the responding subjects who had undergone PET scan evaluation after a single dose of anti-IGF1R, 4 out of 4 subjects had improvement in their PET signal after the single dose of anti-IGF1R. Three out of the 4 subjects had a >25% improvement or decrease in the FDG-PET standardized uptake value, and the 4$^{th}$ subject had a 15% improvement.

Guidelines for Positron Emission Tomography (PET) and Positron Emission Tomography/Computed Tomography (PET/CT)

PET-FDG scans described and discussed herein were performed at various clinical sites that received the following operating guidelines.

All scans will be performed on a dedicated PET or PET/CT scanner (not a dual-headed SPECT scanner). The same PET or PET/CT scanner must be used for all exams for the same subject. Scanner requirements include:

Field of View (FOV) appropriate for body imaging
High resolution and high sensitivity
Post injection transmission capability
Reconstruction algorithms with correction for attenuation, scatter and randoms
Ability to calculate Standardized Uptake Values (SUV)

Subject Preparation

Subjects should receive instruction to avoid strenuous exercise for 24 hours prior to a scheduled FDG-PET or FDG-PET/CT scan.
Subjects will need to fast (except water) for a minimum of 4 hours prior to radiotracer injection.
Subjects are encouraged to maintain well-hydrated status.
For all subjects, perform glucose monitoring (finger-stick glucose acceptable). If glucose>150 mg/dl, reschedule exam with optimization of diabetic control.
Intravenous (IV) injection of radiotracer should be performed via a well functioning IV catheter.
The use of pre-medication to diminish activated brown fat activity may be used as per local site
Immediately before and after radiotracer injection, care should be taken to keep the subject warm and comfortable. The subject should sit or lie in a quiet area during the incubation phase.

Radiopharmaceutical

[$^{18}$F]-fluorodeoxyglucose, (FDG), a glucose analogue, is the only radiotracer that will be used in this study. FDG must be prepared in accordance with the institution's standard procedure or obtained from commercial vendor. The recommended dose of FDG is 10-20 mCi.

Scanning Protocol

Immediately prior to scanning, subjects should be asked to urinate to minimize the chance that they will need to move during the scan.
Baseline scans to be performed approximately 75 minutes (+/−10 minutes) following intravenous injection of radiotracer. The incubation time (time between radiotracer administration and start of emission scan) should be noted for the baseline exam. Follow-up scan incubation time should be within a +/−5-minute window of the baseline exam incubation time.
Scan the whole body to include the skull base to proximal femurs. Repeat sequence of anatomic acquisition (neck to pelvis or pelvis to neck) in standard fashion from time point to time point.
Acquisition time per bed position as per local site protocol, which should be duplicated at each time point.
Perform all scans with attenuation correction.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. A method for treating a Ewing's sarcoma tumor, in a subject, comprising evaluating glucose metabolism of the tumor after the subject has received a first dose of IGF1R inhibitor, but before a second dose of the inhibitor; or within 14 days of a first dose of IGF1R inhibitor but before a second dose of said inhibitor;

wherein treatment with the IGF1R inhibitor is discontinued if glucose metabolism does not significantly decrease or remain constant after said first dose;

and continuing treatment with the IGF1R inhibitor if glucose metabolism does significantly decrease or remain constant after said first dose; wherein the IGF1R inhibitor is an isolated antibody or antigen-binding fragment thereof comprising a light chain immunoglobulin comprising CDR1, CDR2 and CDR3 of an immunoglobulin light chain whose amino acid sequence is set forth in SEQ ID NO: 24; and, a heavy chain immunoglobulin comprising CDR1, CDR2 and CDR3 of an immunoglobulin heavy chain whose amino acid sequence is set forth in SEQ ID NO: 18.

2. The method of claim 1 wherein glucose metabolism is evaluated by administering labeled glucose and monitoring its metabolism by the tumor.

3. The method of claim 2 wherein glucose metabolism is evaluated by $^{18}F$-fluorodeoxyglucose positron emission tomography.

4. The method of claim 1 wherein the Ewing's sarcoma is recurrent or relapsed Ewing's sarcoma.

5. The method of claim 1 wherein the subject is a human.

6. The method of claim 1 comprising continuing treatment with the IGF1R inhibitor if glucose metabolism decreases by about 15% to about 25% after said first dose.

7. The method of claim 1 wherein the IGF1R inhibitor is an isolated antibody.

8. The method of claim 7 wherein the antibody or fragment heavy and/or light chain variable region is linked to an immunoglobulin constant domain.

9. The method of claim 8 wherein immunoglobulin constant domain is selected from the group consisting of: kappa light chain, lambda light chain, gamma-1 heavy chain, gamma-2 heavy chain, gamma-3 heavy chain and gamma-4 heavy chain.

10. The method of claim 1 wherein the subject is administered an IGF1R antibody at a dose of about 1 to about 20 mg/kg every two weeks.

11. The method of claim 1 wherein the subject is administered an IGF1R antibody at a dose of about 10 mg/kg every two weeks.

12. The method of claim 1 wherein the subject is further administered a further chemotherapeutic agent.

13. The method of claim 12 wherein a further chemotherapeutic agent is

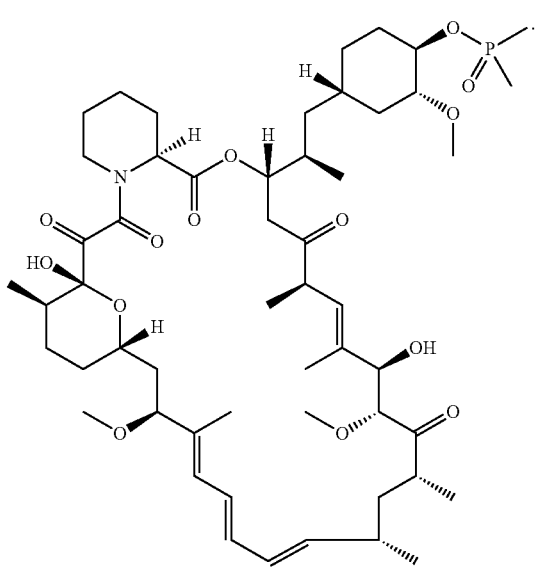

14. The method of claim 12 wherein a further chemotherapeutic agent is exemestane.

15. The method of claim 12 wherein a further chemotherapeutic agent is cyclophosphamide.

16. The method of claim 12 wherein a further chemotherapeutic agent is dactinomycin.

17. The method of claim 12 wherein a further chemotherapeutic agent is doxorubicin.

18. The method of claim 12 wherein a further chemotherapeutic agent is ifosfamide.

19. The method of claim 12 wherein a further chemotherapeutic agent is etoposide.

20. The method of claim 12 wherein a further chemotherapeutic agent is vincristine.

21. The method of claim 12 wherein a further chemotherapeutic agent is topotecan.

\* \* \* \* \*

SEQUENCE LISTING

<160> NUMBER OF SEQ ID NOS: 24

<210> SEQ ID NO 1
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 1

```
atg tcg cca tca caa ctc att ggg ttt ctg ctg ctc tgg gtt cca gcc    48
Met Ser Pro Ser Gln Leu Ile Gly Phe Leu Leu Leu Trp Val Pro Ala
1               5                   10                  15 tcc agg ggt gaa att gtg ctg act cag agc cca gac tct ctg tct gtg    96
```

```
                                                                              144
act cca ggc gag aga gtc acc atc acc tgc cgg gcc agt cag agc att
Thr Pro Gly Glu Arg Val Thr Ile Thr Cys Arg Ala Ser Gln Ser Ile
         35                  40                  45

192
ggt agt agc tta cac tgg tac cag cag aaa cca ggt cag tct cca aag
Gly Ser Ser Leu His Trp Tyr Gln Gln Lys Pro Gly Gln Ser Pro Lys
 50                  55                  60

240
ctt ctc atc aag tat gca tcc cag tcc ctc tca ggg gtc ccc tcg agg
Leu Leu Ile Lys Tyr Ala Ser Gln Ser Leu Ser Gly Val Pro Ser Arg
65                  70                  75                  80

288
ttc agt ggc agt gga tct ggg aca gat ttc acc ctc acc atc agt agc
Phe Ser Gly Ser Gly Ser Gly Thr Asp Phe Thr Leu Thr Ile Ser Ser
                 85                  90                  95

336
ctc gag gct gaa gat gct gca gcg tat tac tgt cat cag agt agt cgt
Leu Glu Ala Glu Asp Ala Ala Ala Tyr Tyr Cys His Gln Ser Ser Arg
            100                 105                 110

384
tta cct cac act ttc ggc caa ggg acc aag gtg gag atc aaa cgt acg
Leu Pro His Thr Phe Gly Gln Gly Thr Lys Val Glu Ile Lys Arg Thr
        115                 120                 125

<210> SEQ ID NO 2
<211> LENGTH: 128
<212> TYPE: PRT
<213> ORGANISM: Homo sapiens

<400> SEQUENCE: 2

Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Ser Leu Ser Val
            20                  25                  30

Thr Pro Gly Glu Arg Val Thr Ile Thr Cys Arg Ala Ser Gln Ser Ile
        35                  40                  45

Gly Ser Ser Leu His Trp Tyr Gln Gln Lys Pro Gly Gln Ser Pro Lys
 50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Ser Ser
                 85                  90                  95

Leu Glu Ala Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 3
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 3

48
atg tcg cca tca caa ctc att ggg ttt ctg ctg ctc tgg gtt cca gcc
Met Ser Pro Ser Gln Leu Ile Gly Phe Leu Leu Leu Trp Val Pro Ala
 1               5                  10                  15

96
tcc agg ggt gaa att gtg ctg act cag agc cca gac tct ctg tct gtg
Ser Arg Gly Glu Ile Val Leu Thr Gln Ser Pro Asp Ser Leu Ser Val
            20                  25                  30

144
act cca ggc gag aga gtc acc atc acc tgc cgg gcc agt cag agc att
Thr Pro Gly Glu Arg Val Thr Ile Thr Cys Arg Ala Ser Gln Ser Ile
```

```
                           35                  40                  45
ggt agt agc tta cac tgg tac cag cag aaa cca ggt cag tct cca aag        192
Gly Ser Ser Leu His Trp Tyr Gln Gln Lys Pro Gly Gln Ser Pro Lys
     50                  55                  60 ctt ctc atc aag tat gca tcc cag tcc ctc tca ggg gtc ccc tcg agg        240
Leu Leu Ile Lys Tyr Ala Ser Gln Ser Leu Ser Gly Val Pro Ser Arg
 65                  70                  75                  80 ttc agt ggc agt gga tct ggg aca gat ttc acc ctc acc atc agt agc        288
Phe Ser Gly Ser Gly Ser Gly Thr Asp Phe Thr Leu Thr Ile Ser Ser
                 85                  90                  95 ctc gag gct gaa gat ttc gca gtg tat tac tgt cat cag agt agt cgt        336
Leu Glu Ala Glu Asp Phe Ala Val Tyr Tyr Cys His Gln Ser Ser Arg
             100                 105                 110 tta cct cac act ttc ggc caa ggg acc aag gtg gag atc aaa cgt acg        384
Leu Pro His Thr Phe Gly Gln Gly Thr Lys Val Glu Ile Lys Arg Thr
         115                 120                 125

<210> SEQ ID NO 4
<211> LENGTH: 128
<212> TYPE: PRT
<213> ORGANISM: Homo sapiens

<400> SEQUENCE: 4

Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Ser Leu Ser Val
             20                  25                  30

Thr Pro Gly Glu Arg Val Thr Ile Thr Cys Arg Ala Ser Gln Ser Ile
         35                  40                  45

Gly Ser Ser Leu His Trp Tyr Gln Gln Lys Pro Gly Gln Ser Pro Lys
     50                  55                  60

Leu Leu Ile Lys Tyr Ala Ser Gln Ser Leu Ser Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Glu Ala Glu Asp Phe Ala Val Tyr Tyr Cys His Gln Ser Ser Arg
             100                 105                 110

Leu Pro His Thr Phe Gly Gln Gly Thr Lys Val Glu Ile Lys Arg Thr
         115                 120                 125

<210> SEQ ID NO 5
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 5 atg tcg cca tca caa ctc att ggg ttt ctg ctg ctc tgg gtt cca gcc        48
Met Ser Pro Ser Gln Leu Ile Gly Phe Leu Leu Leu Trp Val Pro Ala
 1               5                  10                  15 tcc agg ggt gaa att gtg ctg act cag agc cca ggt acc ctg tct gtg        96
Ser Arg Gly Glu Ile Val Leu Thr Gln Ser Pro Gly Thr Leu Ser Val
             20                  25                  30 tct cca ggc gag aga gcc acc ctc tcc tgc cgg gcc agt cag agc att       144
Ser Pro Gly Glu Arg Ala Thr Leu Ser Cys Arg Ala Ser Gln Ser Ile
         35                  40                  45 ggt agc agc tta cac tgg tac cag cag aaa cca ggt cag gct cca agg       192
Gly Ser Ser Leu His Trp Tyr Gln Gln Lys Pro Gly Gln Ala Pro Arg
     50                  55                  60
```

```
ctt ctc atc aag tat gca tcc cag tcc ctc tca ggg atc ccc gat agg       240
Leu Leu Ile Lys Tyr Ala Ser Gln Ser Leu Ser Gly Ile Pro Asp Arg
 65                  70                  75                  80 ttc agt ggc agt gga tct ggg aca gat ttc acc ctc acc atc agt aga       288
Phe Ser Gly Ser Gly Ser Gly Thr Asp Phe Thr Leu Thr Ile Ser Arg
                 85                  90                  95 ctg gag cct gaa gat gct gca gcg tat tac tgt cat cag agt agt cgt       336
Leu Glu Pro Glu Asp Ala Ala Ala Tyr Tyr Cys His Gln Ser Ser Arg
            100                 105                 110 tta cct cac act ttc ggc caa ggg acc aag gtg gag atc aaa cgt aca       384
Leu Pro His Thr Phe Gly Gln Gly Thr Lys Val Glu Ile Lys Arg Thr
        115                 120                 125

<210> SEQ ID NO 6
<211> LENGTH: 128
<212> TYPE: PRT
<213> ORGANISM: Homo sapiens

<400> SEQUENCE: 6

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Ala Ala Ala Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 7
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 7 atg tcg cca tca caa ctc att ggg ttt ctg ctg ctc tgg gtt cca gcc        48
Met Ser Pro Ser Gln Leu Ile Gly Phe Leu Leu Leu Trp Val Pro Ala
1               5                   10                  15 tcc agg ggt gaa att gtg ctg act cag agc cca ggt acc ctg tct gtg        96
Ser Arg Gly Glu Ile Val Leu Thr Gln Ser Pro Gly Thr Leu Ser Val
            20                  25                  30 tct cca ggc gag aga gcc acc ctc tcc tgc cgg gcc agt cag agc att       144
Ser Pro Gly Glu Arg Ala Thr Leu Ser Cys Arg Ala Ser Gln Ser Ile
        35                  40                  45 ggt agt agc tta cac tgg tac cag cag aaa cca ggt cag gct cca agg       192
Gly Ser Ser Leu His Trp Tyr Gln Gln Lys Pro Gly Gln Ala Pro Arg
    50                  55                  60 ctt ctc atc aag tat gca tcc cag tcc ctc tca ggg atc ccc gat agg       240
Leu Leu Ile Lys Tyr Ala Ser Gln Ser Leu Ser Gly Ile Pro Asp Arg
65                  70                  75                  80
```

| | |
|---|---:|
| ttc agt ggc agt gga tct ggg aca gat ttc acc ctc acc atc agt aga<br>Phe Ser Gly Ser Gly Ser Gly Thr Asp Phe Thr Leu Thr Ile Ser Arg<br>                   85                          90                    95 | 288 |
| ctg gag cct gaa gat ttc gca gtg tat tac tgt cat cag agt agt cgt<br>Leu Glu Pro Glu Asp Phe Ala Val Tyr Tyr Cys His Gln Ser Ser Arg<br>               100                      105                    110 | 336 |
| tta cct cac act ttc ggc caa ggg acc aag gtg gag atc aaa cgt aca<br>Leu Pro His Thr Phe Gly Gln Gly Thr Lys Val Glu Ile Lys Arg Thr<br>         115                      120                    125 | 384 |

<210> SEQ ID NO 8
<211> LENGTH: 128
<212> TYPE: PRT
<213> ORGANISM: Homo sapiens

<400> SEQUENCE: 8

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125

<210> SEQ ID NO 9
<211> LENGTH: 411
<212> TYPE: DNA
<213> ORGANISM: Homo sapiens
<220> FEATURE:
<221> NAME/KEY: CDS
<222> LOCATION: (1)..(411)

<400> SEQUENCE: 9

| | |
|---|---:|
| atg gag ttt ggg ctg agc tgg gtt ttc ctt gtt gct ata tta aaa ggt<br>Met Glu Phe Gly Leu Ser Trp Val Phe Leu Val Ala Ile Leu Lys Gly<br>1                 5                   10                 15 | 48 |
| gtc cag tgt gag gtt cag ctg gtg cag tct ggg gga ggc ttg gta aag<br>Val Gln Cys Glu Val Gln Leu Val Gln Ser Gly Gly Gly Leu Val Lys<br>         20                      25                    30 | 96 |
| cct ggg ggg tcc ctg aga ctc tcc tgt gca gcc tct gga ttc acc ttc<br>Pro Gly Gly Ser Leu Arg Leu Ser Cys Ala Ala Ser Gly Phe Thr Phe<br>               35                      40                    45 | 144 |
| agt agc ttt gct atg cac tgg gtt cgc cag gct cca gga aaa ggt ctg<br>Ser Ser Phe Ala Met His Trp Val Arg Gln Ala Pro Gly Lys Gly Leu<br>       50                      55                    60 | 192 |
| gag tgg ata tca gtt att gat act cgt ggt gcc aca tac tat gca gac<br>Glu Trp Ile Ser Val Ile Asp Thr Arg Gly Ala Thr Tyr Tyr Ala Asp<br>65                  70                  75                  80 | 240 |
| tcc gtg aag ggc cga ttc acc atc tcc aga gac aat gcc aag aac tcc<br>Ser Val Lys Gly Arg Phe Thr Ile Ser Arg Asp Asn Ala Lys Asn Ser<br>               85                      90                    95 | 288 |
| ttg tat ctt caa atg aac agc ctg aga gcc gag gac act gct gtg tat | 336 |

| | | | | | | | | | | | | | | |
|---|---|---|---|---|---|---|---|---|---|---|---|---|---|---|
| Leu | Tyr | Leu | Gln | Met | Asn | Ser | Leu | Arg | Ala | Glu | Asp | Thr | Ala | Val | Tyr |
| | | | 100 | | | | | 105 | | | | 110 | | |

```
tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
        115                 120                 125 caa ggg acc acg gtc acc gtc tcc tca                                  411
Gln Gly Thr Thr Val Thr Val Ser Ser
130                 135

<210> SEQ ID NO 10
<211> LENGTH: 137
<212> TYPE: PRT
<213> ORGANISM: Homo sapiens

<400> SEQUENCE: 10

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 11
<211> LENGTH: 411
<212> TYPE: DNA
<213> ORGANISM: Homo sapiens
<220> FEATURE:
<221> NAME/KEY: CDS
<222> LOCATION: (1)..(411)

<400> SEQUENCE: 11 atg gag ttt ggg ctg agc tgg gtt ttc ctt gtt gct ata tta aaa ggt      48
Met Glu Phe Gly Leu Ser Trp Val Phe Leu Val Ala Ile Leu Lys Gly
1               5                   10                  15 gtc cag tgt gag gtt cag ctg gtg cag tct ggg gga ggc ttg gta cag      96
Val Gln Cys Glu Val Gln Leu Val Gln Ser Gly Gly Gly Leu Val Gln
            20                  25                  30 ccc ggg ggg tcc ctg aga ctc tcc tgt gca gcc tct gga ttc acc ttc     144
Pro Gly Gly Ser Leu Arg Leu Ser Cys Ala Ala Ser Gly Phe Thr Phe
        35                  40                  45 agt agc ttt gct atg cac tgg gtt cgc cag gct cca gga aaa ggt ctg     192
Ser Ser Phe Ala Met His Trp Val Arg Gln Ala Pro Gly Lys Gly Leu
    50                  55                  60 gag tgg ata tca gtt att gat act cgt ggt gcc aca tac tat gca gac     240
Glu Trp Ile Ser Val Ile Asp Thr Arg Gly Ala Thr Tyr Tyr Ala Asp
65                  70                  75                  80 tcc gtg aag ggc cga ttc acc atc tcc aga gac aat gcc aag aac tcc     288
Ser Val Lys Gly Arg Phe Thr Ile Ser Arg Asp Asn Ala Lys Asn Ser
                85                  90                  95
```

```
ttg tat ctt caa atg aac agc ctg aga gcc gag gac act gct gtg tat      336
Leu Tyr Leu Gln Met Asn Ser Leu Arg Ala Glu Asp Thr Ala Val Tyr
        100                 105                 110 tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
            115                 120                 125 caa ggg acc acg gtc acc gtc tcc tca                                  411
Gln Gly Thr Thr Val Thr Val Ser Ser
        130                 135

<210> SEQ ID NO 12
<211> LENGTH: 137
<212> TYPE: PRT
<213> ORGANISM: Homo sapiens

<400> SEQUENCE: 12

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135

<210> SEQ ID NO 13
<211> LENGTH: 119
<212> TYPE: PRT
<213> ORGANISM: Artificial Sequence
<220> FEATURE:
<223> OTHER INFORMATION: Ig

<400> SEQUENCE: 13

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Arg Asn Tyr
            20                  25                  30

Ala Met Tyr Trp Val Arg Gln Ala Pro Gly Lys Gly Leu Glu Trp Val
        35                  40                  45

Ser Ala Ile Gly Ser Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Ala Pro Asn Trp Gly Ser Asp Ala Phe Asp Ile Trp Gly Gln Gly
            100                 105                 110

Thr Met Val Thr Val Ser Ser
```

-continued

```
<210> SEQ ID NO 14
<211> LENGTH: 118
<212> TYPE: PRT
<213> ORGANISM: Artificial Sequence
<220> FEATURE:
<223> OTHER INFORMATION: Ig.

<400> SEQUENCE: 14

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 15
<211> LENGTH: 125
<212> TYPE: PRT
<213> ORGANISM: Artificial Sequence
<220> FEATURE:
<223> OTHER INFORMATION: Ig.

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Thr Thr Phe Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Gly Trp Ser Asp Ser Tyr Tyr Tyr Tyr Gly Met
            100                 105                 110

Asp Val Trp Gly Gln Gly Thr Thr Val Thr Val Ser Ser
        115                 120                 125

<210> SEQ ID NO 16
<211> LENGTH: 130
<212> TYPE: PRT
<213> ORGANISM: Artificial Sequence
<220> FEATURE:
<223> OTHER INFORMATION: Ig.

<400> SEQUENCE: 16
```

```
Glu Val Gln Leu Val Gln Ser Gly Ala Glu Val Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Leu Arg Phe Leu Glu Trp Ser Thr Gln Asp His Tyr
            100                 105                 110

Tyr Tyr Tyr Tyr Met Asp Val Trp Gly Lys Gly Thr Thr Val Thr Val
            115                 120                 125

Ser Ser
    130

<210> SEQ ID NO 17
<211> LENGTH: 119
<212> TYPE: PRT
<213> ORGANISM: Artificial Sequence
<220> FEATURE:
<223> OTHER INFORMATION: Ig.

<400> SEQUENCE: 17

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Thr Gly Arg Thr Asp Ala Phe Asp Ile Trp Gly Gln Gly
            100                 105                 110

Thr Trp Val Thr Val Ser Ser
    115

<210> SEQ ID NO 18
<211> LENGTH: 117
<212> TYPE: PRT
<213> ORGANISM: Artificial Sequence
<220> FEATURE:
<223> OTHER INFORMATION: Ig.

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Gly Gly
            20                  25                  30

Tyr Leu Trp Asn Trp Ile Arg Gln Pro Pro Gly Lys Gly Leu Glu Trp
        35                  40                  45
```

```
Ile Gly Tyr Ile Ser Tyr Asp Gly Thr Asn Asn Tyr Lys Pro Ser Leu
        50                  55                  60

Lys Asp Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Tyr Gly Arg Val Phe Phe Asp Tyr Trp Gly Gln Gly Thr Leu
                100                 105                 110

Val Thr Val Ser Ser
            115

<210> SEQ ID NO 19
<211> LENGTH: 107
<212> TYPE: PRT
<213> ORGANISM: Artificial Sequence
<220> FEATURE:
<223> OTHER INFORMATION: Ig.

<400> SEQUENCE: 19

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Pro
                85                  90                  95

Thr Phe Gly Pro Gly Thr Lys Val Asp Ile Lys
                100                 105

<210> SEQ ID NO 20
<211> LENGTH: 108
<212> TYPE: PRT
<213> ORGANISM: Artificial Sequence
<220> FEATURE:
<223> OTHER INFORMATION: Ig.

<400> SEQUENCE: 20

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Lys Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
                100                 105

<210> SEQ ID NO 21
<211> LENGTH: 109
```

```
<212> TYPE: PRT
<213> ORGANISM: Artificial Sequence
<220> FEATURE:
<223> OTHER INFORMATION: Ig.

<400> SEQUENCE: 21

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu His Arg Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Cys
                85                  90                  95

Ser Phe Gly Gln Gly Thr Lys Leu Glu Ile Lys Arg Thr
            100                 105

<210> SEQ ID NO 22
<211> LENGTH: 109
<212> TYPE: PRT
<213> ORGANISM: Artificial Sequence
<220> FEATURE:
<223> OTHER INFORMATION: Ig.

<400> SEQUENCE: 22

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Thr Trp Tyr Gln Gln Lys Pro Gly Gln Ala Pro Ile Leu Val Ile Tyr
        35                  40                  45

Gly Glu Asn Lys Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Lys Ser Arg Asp Gly Ser Gly Gln His
                85                  90                  95

Leu Val Phe Gly Gly Gly Thr Lys Leu Thr Val Leu Gly
            100                 105

<210> SEQ ID NO 23
<211> LENGTH: 112
<212> TYPE: PRT
<213> ORGANISM: Artificial Sequence
<220> FEATURE:
<223> OTHER INFORMATION: Ig.

<400> SEQUENCE: 23

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60
```

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Thr His Trp Pro Leu Thr Phe Gly Gln Gly Thr Lys Val Glu Ile Lys
            100                 105                 110

<210> SEQ ID NO 24
<211> LENGTH: 112
<212> TYPE: PRT
<213> ORGANISM: Artificial Sequence
<220> FEATURE:
<223> OTHER INFORMATION: Ig.

<400> SEQUENCE: 24

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Ile Val His Ser
                 20                  25                  30

Asn Gly Asn Thr Tyr Leu Gln Trp Tyr Leu Gln Lys Pro Gly Gln Ser
             35                  40                  45

Pro Gln Leu Leu Ile Tyr Lys Val Ser Asn Arg Leu Tyr Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Trp Thr Phe Gly Gln Gly Thr Lys Val Glu Ile Lys
            100                 105                 110
```